United States Patent
Cincotta

(10) Patent No.: US 12,357,693 B2
(45) Date of Patent: *Jul. 15, 2025

(54) METHOD FOR INDUCING TUMOR REGRESSION

(71) Applicant: VeroScience LLC, Tiverton, RI (US)

(72) Inventor: Anthony H. Cincotta, Tiverton, RI (US)

(73) Assignee: VeroScience LLC, Tiverton, RI (US)

( * ) Notice: Subject to any disclaimer, the term of this patent is extended or adjusted under 35 U.S.C. 154(b) by 243 days.

This patent is subject to a terminal disclaimer.

(21) Appl. No.: 17/752,676

(22) Filed: May 24, 2022

(65) Prior Publication Data

US 2022/0288209 A1 Sep. 15, 2022

Related U.S. Application Data

(63) Continuation of application No. 17/030,068, filed on Sep. 23, 2020, now Pat. No. 11,607,455.

(60) Provisional application No. 62/904,430, filed on Sep. 23, 2019.

(51) Int. Cl.
| | | |
|---|---|---|
| A61K 41/00 | (2020.01) | |
| A61K 31/336 | (2006.01) | |
| A61K 31/519 | (2006.01) | |
| A61P 35/00 | (2006.01) | |

(52) U.S. Cl.
CPC ........ *A61K 41/0057* (2013.01); *A61K 31/336* (2013.01); *A61K 31/519* (2013.01); *A61P 35/00* (2018.01)

(58) Field of Classification Search
CPC .............. A61K 41/0057; A61K 31/336; A61K 31/519; A61P 35/00
See application file for complete search history.

(56) References Cited

U.S. PATENT DOCUMENTS

| | | | |
|---|---|---|---|
| 941,005 A | 11/1909 | Brandt | |
| 3,752,814 A | 8/1973 | Fluckiger | |
| 4,654,345 A | 3/1987 | Cavanak | |
| 4,659,715 A | 4/1987 | Meier et al. | |
| 4,749,709 A | 6/1988 | Meier et al. | |
| 4,783,469 A | 11/1988 | Meier et al. | |
| 4,962,197 A | 10/1990 | Foley et al. | |
| 5,006,526 A | 4/1991 | Meier et al. | |
| 5,066,495 A | 11/1991 | Moro et al. | |
| 5,186,420 A | 2/1993 | Beauchamp et al. | |
| 5,344,832 A | 9/1994 | Cincotta et al. | |
| 5,468,755 A | 11/1995 | Cincotta et al. | |
| 5,496,803 A | 3/1996 | Meier et al. | |
| 5,523,082 A | 6/1996 | Corbiere | |
| 5,554,623 A | 9/1996 | Cincotta et al. | |
| 5,565,454 A | 10/1996 | Cincotta | |
| 5,585,347 A | 12/1996 | Meier et al. | |
| 5,626,860 A | 5/1997 | Cincotta et al. | |
| 5,635,512 A | 6/1997 | Cincotta et al. | |
| 5,654,313 A | 8/1997 | Cincotta et al. | |
| 5,668,155 A | 9/1997 | Cincotta et al. | |
| 5,679,685 A | 10/1997 | Cincotta et al. | |
| 5,688,794 A | 11/1997 | Meier et al. | |
| 5,696,128 A | 12/1997 | Meier et al. | |
| 5,700,795 A | 12/1997 | Meier et al. | |
| 5,700,800 A | 12/1997 | Cincotta et al. | |
| 5,712,265 A | 1/1998 | Meier et al. | |
| 5,714,519 A | 2/1998 | Cincotta et al. | |
| 5,716,932 A | 2/1998 | Meier et al. | |
| 5,716,933 A | 2/1998 | Meier et al. | |
| 5,716,957 A | 2/1998 | Cincotta et al. | |
| 5,716,962 A | 2/1998 | Cincotta et al. | |
| 5,719,160 A | 2/1998 | Cincotta et al. | |
| 5,731,287 A | 3/1998 | Meier et al. | |
| 5,731,312 A | 3/1998 | Cincotta et al. | |
| 5,741,503 A | 4/1998 | Cincotta et al. | |
| 5,744,477 A | 4/1998 | Meier et al. | |
| 5,750,519 A | 5/1998 | Cincotta et al. | |
| 5,756,513 A | 5/1998 | Meier et al. | |
| 5,760,047 A | 6/1998 | Meier et al. | |
| 5,792,748 A | 8/1998 | Meier et al. | |
| 5,814,638 A | 9/1998 | Lee et al. | |
| 5,830,895 A | 11/1998 | Cincotta et al. | |
| 5,854,255 A | 12/1998 | Cincotta et al. | |
| 5,866,584 A | 2/1999 | Cincotta et al. | |
| 5,872,127 A | 2/1999 | Meier et al. | |
| 5,872,133 A | 2/1999 | Meier et al. | |
| 5,877,183 A | 3/1999 | Cincotta | |
| 5,902,811 A | 5/1999 | Cincotta | |
| 5,905,083 A | 5/1999 | Meier et al. | |

(Continued)

FOREIGN PATENT DOCUMENTS

| | | |
|---|---|---|
| CA | 2166204 | 4/2009 |
| CN | 102283844 | 6/2014 |

(Continued)

OTHER PUBLICATIONS

Hendrzak-Henion et al (Year: 1999).*
Fan et al (Year: 1995).*
Alkarakooly et al., "Metabolic reprogramming by Dichloroacetic acid potentiates photodynamic therapy of human breast adenocarcinoma MCF-7 cells," PLOS One, Oct. 23, 2018, 13(10):e0206182.
Liu et al., "EtNBSe-PDT inhibited proliferation and induced autophagy of HNE-1 cells via downregulating the Wnt/beta-catenin signaling pathway," Photodiagnosis and Photodynamic Therapy, Mar. 1, 2019, 26:65-72.
[No Author Listed], "Dissolution," General Chapter 711, U.S. Pharmacopoeia (USP), 34th ed., Dec. 1, 2011, 8 pages.

(Continued)

*Primary Examiner* — Jeffrey S Lundgren
*Assistant Examiner* — Ibrahim D Bori
(74) *Attorney, Agent, or Firm* — Fish & Richardson P.C.

(57) ABSTRACT

Methods for treating cancer and/or inducing tumor regression in mammals (e.g., humans) by increasing the metabolism of the mammal, administering a BA dye to the mammal, and thereafter exposing the tumor to actinic light for activation of the BA dye.

20 Claims, 6 Drawing Sheets

(56) References Cited

U.S. PATENT DOCUMENTS

| | | |
|---|---|---|
| 5,952,329 A | 9/1999 | Cincotta et al. |
| 6,004,972 A | 12/1999 | Meier et al. |
| 6,071,914 A | 6/2000 | Meier et al. |
| 6,075,020 A | 6/2000 | Meier et al. |
| 6,855,707 B2 | 2/2005 | Cincotta |
| 7,888,310 B2 | 2/2011 | Cincotta |
| 8,021,681 B2 | 9/2011 | Cincotta |
| 8,137,992 B2 | 3/2012 | Cincotta |
| 8,137,993 B2 | 3/2012 | Cincotta |
| 8,137,994 B2 | 3/2012 | Cincotta |
| 8,431,155 B1 | 4/2013 | Cincotta et al. |
| 8,613,947 B2 | 12/2013 | Cincotta et al. |
| 8,741,918 B2 | 6/2014 | Cincotta |
| 8,821,915 B2 | 9/2014 | Cincotta |
| 8,877,708 B2 | 11/2014 | Cincotta |
| 9,192,576 B2 | 11/2015 | Cincotta et al. |
| 9,205,084 B2 | 12/2015 | Cincotta |
| 9,352,025 B2 | 5/2016 | Cincotta |
| 9,364,515 B2 | 6/2016 | Cincotta |
| 9,415,005 B2 | 8/2016 | Cincotta |
| 9,522,117 B2 | 12/2016 | Cincotta et al. |
| 9,655,865 B2 | 5/2017 | Cincotta |
| 9,700,555 B2 | 7/2017 | Cincotta et al. |
| 9,895,422 B2 | 2/2018 | Cincotta |
| 9,925,186 B2 | 3/2018 | Cincotta |
| 9,993,474 B2 | 6/2018 | Cincotta et al. |
| 9,999,653 B2 | 6/2018 | Cincotta |
| 10,137,132 B2 | 11/2018 | Cincotta |
| 10,238,653 B2 | 3/2019 | Cincotta |
| 10,307,421 B2 | 6/2019 | Cincotta et al. |
| 10,675,282 B2 | 6/2020 | Cincotta |
| 10,688,094 B2 | 6/2020 | Cincotta et al. |
| 10,688,155 B2 | 6/2020 | Cincotta |
| 10,894,791 B2 | 1/2021 | Cincotta |
| 11,000,522 B2 | 5/2021 | Cincotta et al. |
| 11,045,464 B2 | 6/2021 | Cincotta |
| 11,241,429 B2 | 2/2022 | Cincotta |
| 11,510,921 B2 | 11/2022 | Cincotta |
| 11,560,375 B2 | 1/2023 | Cincotta |
| 11,607,455 B2 | 3/2023 | Cincotta |
| 11,666,567 B2 | 6/2023 | Cincotta et al. |
| 11,878,974 B2 | 1/2024 | Cincotta |
| 11,883,399 B2 | 1/2024 | Cincotta |
| 2001/0016582 A1 | 8/2001 | Cincotta |
| 2001/0049350 A1 | 12/2001 | Cincotta et al. |
| 2002/0146400 A1 | 10/2002 | Cincotta |
| 2002/0187985 A1 | 12/2002 | Cincotta |
| 2002/0197262 A1 | 12/2002 | Hasan et al. |
| 2004/0028613 A1 | 2/2004 | Quay |
| 2004/0077679 A1 | 4/2004 | Cincotta |
| 2004/0081678 A1 | 4/2004 | Cincotta |
| 2004/0102383 A1 | 5/2004 | Cincotta et al. |
| 2004/0220190 A1 | 11/2004 | Cincotta |
| 2005/0054652 A1 | 3/2005 | Cincotta |
| 2005/0054734 A1 | 3/2005 | Cincotta |
| 2005/0079203 A1 | 4/2005 | Cincotta |
| 2005/0215558 A1 | 9/2005 | Cincotta |
| 2006/0258589 A1 | 11/2006 | McTavish |
| 2007/0004617 A1 | 1/2007 | Tsai |
| 2008/0200453 A1 | 8/2008 | Cincotta |
| 2008/0293735 A1 | 11/2008 | Cincotta |
| 2009/0110674 A1 | 4/2009 | Loizou |
| 2009/0137598 A1 | 5/2009 | Cincotta |
| 2009/0137599 A1 | 5/2009 | Cincotta |
| 2009/0143390 A1 | 6/2009 | Cincotta |
| 2010/0035886 A1 | 2/2010 | Nivorozhkin et al. |
| 2011/0136817 A1 | 6/2011 | Cincotta |
| 2011/0195970 A1 | 8/2011 | Cincotta |
| 2011/0195971 A1 | 8/2011 | Cincotta |
| 2012/0129783 A1 | 5/2012 | Cincotta |
| 2012/0142582 A1 | 6/2012 | Cincotta |
| 2012/0323163 A1 | 12/2012 | Chen et al. |
| 2013/0197005 A1 | 8/2013 | Cincotta |
| 2013/0274246 A1 | 10/2013 | Cincotta |
| 2013/0287848 A1 | 10/2013 | Cincotta et al. |
| 2014/0011776 A1 | 1/2014 | Vassillou et al. |
| 2014/0031359 A1 | 1/2014 | Cincotta |
| 2014/0051685 A1 | 2/2014 | Cincotta |
| 2014/0187560 A1 | 7/2014 | Cincotta et al. |
| 2014/0249136 A1 | 9/2014 | Cincotta |
| 2014/0275235 A1 | 9/2014 | Deleyrolle et al. |
| 2014/0342975 A1 | 11/2014 | Cincotta |
| 2015/0011554 A1 | 1/2015 | Cincotta et al. |
| 2015/0024995 A1 | 1/2015 | Cincotta |
| 2015/0335641 A1 | 11/2015 | Cincotta |
| 2016/0032488 A1 | 2/2016 | Takahashi et al. |
| 2016/0038424 A1 | 2/2016 | Cincotta et al. |
| 2016/0263181 A1 | 9/2016 | Cincotta |
| 2016/0271222 A1 | 9/2016 | Cincotta |
| 2016/0324848 A1 | 11/2016 | Cincotta |
| 2017/0020871 A1 | 1/2017 | Cincotta et al. |
| 2017/0209539 A1 | 7/2017 | Cincotta |
| 2017/0305898 A1 | 10/2017 | Cincotta |
| 2017/0340271 A1 | 11/2017 | Cincotta |
| 2017/0340632 A1 | 11/2017 | Cincotta et al. |
| 2018/0051019 A1 | 2/2018 | Cincotta |
| 2018/0125843 A1 | 5/2018 | Cincotta |
| 2018/0140675 A1 | 5/2018 | Cincotta |
| 2018/0177874 A1 | 6/2018 | Cincotta |
| 2018/0263978 A1 | 9/2018 | Cincotta et al. |
| 2019/0054046 A1 | 2/2019 | Singh et al. |
| 2019/0160059 A1 | 5/2019 | Cincotta et al. |
| 2019/0167677 A1 | 6/2019 | Cincotta |
| 2019/0343833 A1 | 11/2019 | Cincotta et al. |
| 2020/0253970 A1 | 8/2020 | Cincotta |
| 2020/0276193 A1 | 9/2020 | Cincotta et al. |
| 2021/0085787 A1 | 3/2021 | Cincotta et al. |
| 2021/0094946 A1 | 4/2021 | Cincotta |
| 2021/0130344 A1 | 5/2021 | Cincotta |
| 2021/0177839 A1 | 6/2021 | Cincotta |
| 2021/0228576 A1 | 7/2021 | Cincotta et al. |
| 2021/0401824 A1 | 12/2021 | Cincotta |
| 2022/0125379 A1 | 4/2022 | Cincotta |
| 2022/0142960 A1 | 5/2022 | Cincotta et al. |
| 2022/0265648 A1 | 8/2022 | Cincotta |
| 2023/0150999 A1 | 5/2023 | Cincotta |
| 2023/0263892 A1 | 8/2023 | Cincotta |
| 2023/0286974 A1 | 9/2023 | Cincotta |
| 2023/0321090 A1 | 10/2023 | Cincotta |
| 2024/0131026 A1 | 4/2024 | Cincotta et al. |

FOREIGN PATENT DOCUMENTS

| | | |
|---|---|---|
| CN | 102727894 | 10/2015 |
| GB | 2192541 | 1/1988 |
| JP | H02-121919 | 5/1990 |
| JP | 2021-500357 | 1/2021 |
| WO | WO 2002/083141 | 10/2002 |
| WO | WO 2009/091576 | 7/2009 |
| WO | WO 2013/165902 | 11/2013 |
| WO | WO 2017/184875 | 10/2017 |
| WO | WO 2020/011854 A1 | 1/2020 |
| WO | WO 2021/019231 A1 | 2/2021 |

OTHER PUBLICATIONS

Berge et al., "Pharmaceutical Salts," Journal of Pharmaceutical Sciences, 1977, 66(1):1-19.
Dietrich et al., "Non-alcoholic fatty liver disease, obesity and the metabolic syndrome," Best Practice & Research Clinical Gastroenterology, 2014, 28:637-653.
EP Extended European Search Report in European Appln No. 18868516.8, dated Jun. 29, 2021, 8 pages.
Gould, "Salt selection for basic drugs," International Journal of Pharmaceutics, 1986, 33:201-217.
Pan, "Industrial Pharmaceutics," China Medical Science and Technology Press, the first printing of the 3rd edition, Aug. 2015, p. 47 (Partial English Translation only).
PCT International Preliminary Report on Patentability in International Appln PCT/US2018/056554, dated Apr. 21, 2020, 15 pages.
PCT International Search Report and Written Opinion in Application No. PCT/US2017/028656, mailed on Jul. 7, 2017, 13 pages.

(56) References Cited

OTHER PUBLICATIONS

PCT International Search Report and Written Opinion in International Appl. PCT/US2018/056554, dated, Jan. 3, 2019, 17 pages.
Pukngam et al., "Development and Validation of a Stability-Indicating HPLC Method for Determination of Bromocriptine Mesylate in Bulk Drug and Tablets," Current Pharmaceutical Analysis, 2013, 9:92-101.
Rathbone et al., academia.edu [Online], "Modified-Release Drug Delivery Technology," Marcel Dekker, Inc., 2003, [Retrieved on Nov. 23, 2018], retrieved from: URL<https:www.academia.edu/28583222/Modified-Release Drug Delivery Technology?auto=downloade>, 90 pages.
Rowe et al., "Mannitol," Handbook of Pharmaceutical Excipients, 7th ed., 2012, 479-482.
Rowe et al., "Stearic Acid," Handbook of Pharmaceutical Excipients, 6th ed, 2009, 697-699.
Singh et al., "Dosage Forms: Non-Parenteral," Encyclopedia of Pharmaceutical Technology, 2008, 749-761.
Stahl et al., "Pharmaceutical Salts: Properties, Selection, and Use," Wiley-VCH, IUPAC, 2002, 329-345.
Vicchi et al., "Dopaminergic drugs in type 2 diabetes and glucose homeostasis," Pharmacological Research, 2016, 109:74-80.
Granchi et al., "Anti-cancer agents counteracting tumor glycolysis," ChemMedChem, Aug. 2012, 7(8):1318-1350.
Sun et al., "Neutrophils as inflammatory and immune effectors in photodynamic therapy-treated mouse SCCVII tumors," Photochem. Photobiol. Science, Jul. 16, 2002, 1:690-695.
International Preliminary Report on Patentability in International Appln. No. PCT/US2017/028656, mailed on Oct. 23, 2018, 6 pages.
International Preliminary Report on Patentability in International Appln. No. PCT/US2020/052278, dated Mar. 15, 2022, 7 pages.
Office Action in Japanese Appln. No. 2023-018110, mailed on Apr. 2, 2024, 5 pages (with English translation).
Ashton et al., "Oxidative Phosphorylation as an Emerging Target in Cancer Therapy," Clinical Cancer Research, 2018, 24(11):2482-2490.
Cincotta et al., "Novel benzophenothiazinium photosensitizers: preliminary in-vivo results," Photodynamic Therapy: Mechanisms II, SPIE, 1990, 1203:202-210.
Cincotta et al., "Novel Phenothiazinium Photosensitizers for Photodynamic Therapy," SPIE Proceedings, Advances in Photochemotherapy, 1988, 997:145-153.
Cincotta et al., "Novel Photodynamic Effects of a Benzophenothiazine on Two Different Murine Sarcomas," Cancer Research, Mar. 1, 1994, 54:1249-1258.
Cincotta et al., "Novel red absorbing benzo[a]phenoxazinium and benzo[a]phenothiazinium photosensitizers: in vitro evaluation," PhotoChemistry and PhotoBiology, Nov. 1987, 46(5):751-758.
Cincotta et al., "Phototoxicity, Redox Behavior, and Pharmacokinetics of Benzophenoxazine Analogues in EMT-6 Murine Sarcoma Cells," Cancer Research, Jun. 1, 1993, 53:2571-2580.
Deni et al., "Glucose-functionalized amino-OPEs as biocompatible photosensitizers in PDT," European Journal of Medicinal Chemistry, Jan. 28, 2016, 11:58-71.
Fadlan et al., "Synthesis, photophysical properties, and photodynamic activity of positional isomers of TFPP-glucose conjugates," Bioorganic & Medicinal Chemistry, Feb. 19, 2018, 26(8):1848-1858.
Fadok et al., "Differential effects of apoptotic versus lysed cells on macrophage production of cytokines: roles of proteases," Journal of Immunology, 2001, 166:6847-6854.
Fan et al., "Hyperglycemia enhances the effectiveness of PDT," Proceedings of SPIE, 1995, 2392:36-39.
Feng et al., "Energy metabolism targeted drugs synergize with photodynamic therapy to potentiate breast cancer cell death," Photochemical & Photobiological Science, Oct. 9, 2014, 13:1792-1803.
Foley et al., "Structure and Properties of Novel Benzo[α]Phenoxazinium Photochemotherapeutic Agents," SPIE Proceedings, New Directions in Photodynamic Therapy, 1987, 847:90-95.

Foultier et al., "Photosensitization of L12 10 leukemic cells by argon laser irradiation after incubation with haematoporphyrin derivative and rhodamine 123," J Photochem. Photobiol. B: Biol. 1991, 10:119-132.
Granchi et al., "Anti-cancer agents counteracting tumor glycolsis," ChemMedChem, Aug. 2012, 7(8):1318-1350.
Hayashi et al., "A Novel Photodynamic Therapy Targeting Cancer Cells and Tumor-Associated Macrophages," Molecular Cancer Therapeutics, 2015, 14(2):452-460.
Hendrzak-Henion et al., "Role of the immune system in mediating the antitumor effect of benzophenothiazine photodynamic therapy," Photochemistry and Photobiology, 1999, 69(5):575-581.
Lin et al., "Lysosomal Localization and Mechanism of Uptake of Nile Blue Photosensitizers in Tumor Cells," Cancer Research, 1991, 51:2710-2719.
Lin et al., "Photosensitization, Uptake, and Retention of Phenoxazine Nile Blue Derivatives in Human Bladder Carcinoma Cells," Cancer Research, 1991, 51:1109-1116.
Martin et al., "A concomitant ATP-depleting strategy markedly enhances anticancer agent activity," Apoptosis, 2001, 6(1/2):125-131.
Nelson et al., "Glucose administration combined with photodynamic therapy of cancer improves therapeutic efficacy," Lasers in Surgery and Medicine, 1992, 12:153-158.
Nishie et al., "Excellent antitumor effects for gastrointestinal cancers using photodynamic therapy with a novel glucose conjugated chlorin e6," Biochemical and Biophysical Research Communications, Jan. 2018, 496(4):1204-1209.
Oberdanner et al., "Glucose is Required to Maintain High ATP-levels for the Energy-utilizing Steps During PDT-induced Apoptosis," Photochemistry and Photobiology, 2002, 76(6):695-703.
Osinsky et al., "Tumour pH under induced hyperglycemia and efficacy of chemotherapy," Anticancer Research, 1987, 7(2):199-201.
PCT International Search Report and Written Opinion in International Appln. No. PCT/US2020/052278, dated Feb. 10, 2021, 9 pages.
Pelicano et al., "Glycolysis inhibition for anticancer treatment," Oncogene, 2006, 25:4633-4646.
Ramu et al., "Glucose-appended platinum(II)-BODIPY conjugates for targeted photodynamic therapy in red light," Inorganic Chemistry, Feb. 5, 2018, 57(4):1717-1726.
Reiter et al., "Cutting edge: differential effect of apoptotic versus necrotic tumor cells on macrophage antitumor activities," Journal of Immunology, 1999, 163:1730-1732.
Sauter et al., "Consequences of cell death: exposure to necrotic tumor cells, but not primary tissue cells or apoptotic cells, induces the maturation of immunostimulatory dendritic cells," Journal of Experimental Medicine, Feb. 7, 2000, 191(3):423-433.
Sun et al., "Neutrphils as inflammatory and immune effectors in photodynamic therapy-treated mouse SCCVII tumors," Photochem. Photobiol. Science, Jul. 16, 2002, 1:690-695.
Uruma et al., "Synthesis and biological evaluation of glucose conjugated phthalocyanine as a second-generation photosensitizer," Bioorganic & Medicinal Chemistry, Jun. 4, 2019, 27:3279-3284.
Detty et al., "Current clinical and preclinical photosensitizers for use in photodynamic therapy," Journal of Medicinal Chemistry, 2004, 47(16):3897-3915.
Frimberger et al., "Photodynamic Therapy of Naturally Occurring Tumors in Animals Using a Novel Benzophenothiazine Photosensitizer," Clinical Cancer Research, 1998, 4:2207-2218.
Office Action in European Appln No. 21189773.1, mailed on Sep. 16, 2024, 5 pages.
Dolmans et al., "Photodynamic therapy for cancer," Nat Rev Cancer, May 2003, 3(5):380-387.
Bergamaschi et al., "Impact of enzymatic and alkaline hydrolysis on CBD concentration in urine," Anal Bioanal Chem, May 2013, available online Mar. 15, 2013, 405(14):4679-4689 (Author Manuscript, 19 pages).
fda.gov [online], "Data Standards Manual (monographs)," Feb. 27, 2018, retrieved on Jan. 15, 2025, retrieved from URL<https://www.fda.gov/drugs/electronic-regulatory-submission-and-review/data-standards-manual-monographs>, 1 page.

(56) References Cited

OTHER PUBLICATIONS

Giron-Forest et al., "Bromocriptine Methanesulphonate", Analytical Profiles of Drug Substances, 1979, vol. 8, pp. 47-81 (Abstract Only).

Hurd et al., "Cannabidiol for the Reduction of Cue-Induced Craving and Anxiety in Drug-Abstinent Individuals With Heroin Use Disorder: A Double-Blind Randomized Placebo-Controlled Trial," Am J Psychiatry, Nov. 1, 2019, available online May 21, 2019, 176(11):911-922.

Hurd et al., "Early Phase in the Development of Cannabidiol as a Treatment for Addiction: Opioid Relapse Takes Initial Center Stage," Neurotherapeutics, Oct. 2015, 12(4):807-815.

Hurd, "Leading the Next CBD Wave-Safety and Efficacy," JAMA Psychiatry, Apr. 1, 2020, 77(4):341-342.

International Preliminary Report on Patentability in International Appln. No. PCT/US2023/026236, mailed on Jan. 2, 2025, 11 pages.

International Search Report in International Appln. No. PCT/US2023/026236, mailed on Jan. 10, 2024, 15 pages.

Invitation to Pay Additional Fees and, Where Applicable, Protest Fee in International Appln. No. PCT/US2023/026236, mailed on Sep. 28, 2023, 2 pages.

Manini et al., "Safety and pharmacokinetics of oral cannabidiol when administered concomitantly with intravenous fentanyl in humans," J Addict Med, May-Jun. 2015, 9(3):204-210 (Author Manuscript, 17 pages).

Office Action (Notification of Reexamination) in Chinese Appln. No. 201780038243.6, mailed on Jan. 14, 2025, 22 pages (with English translation).

Ren et al., "Cannabidiol, a nonpsychotropic component of cannabis, inhibits cue-induced heroin seeking and normalizes discrete mesolimbic neuronal disturbances," J Neurosci, Nov. 25, 2009, 29(47): 14764-14769.

Tavares et al., "Mucuna pruiens treatment shows anti-obesity and intestinal health effects in obese rats," Food & Function, Feb. 25, 2021, 12(11): 6479-6489 (Accepted Manuscript, 13 pages).

Tsai et al., "Bromocriptine (B) plus Curcumin (C) Synergize to Reduce Nonalcoholic Steatohepatitis (NASH) in Mice," Diabetes, Jun. 1, 2019, 68(Supplement_1):1850-P.

Tsai et al., "Bromocriptine (B) plus Curcumin(C) Interact to Reduce Advanced Fibrosis in a Mouse Methionine-Choline Deficient (MCD) Diet Model of Nonalcoholic Steatohepatitis (NASH)," Diabetes, Jun. 1, 2019, 68(Supplement_1):1851-P.

Tsai et al., Bromocriptone (BC) Improves Hepatic Steatosis, Inflammation, and ER Stress in a Mouse Obesogenic Dietary Model of Nonalcoholic Steatohepatitis (NASH), Diabetes, Jun. 1, 2019, 68(Supplement_1):1868-P.

* cited by examiner

METHOD FOR INDUCING TUMOR REGRESSION

CROSS-REFERENCE TO RELATED APPLICATIONS

This application is a continuation application of U.S. application Ser. No. 17/030,068, filed Sep. 23, 2020 and claims the benefit of priority to U.S. Provisional Application No. 62/904,430, filed on Sep. 23, 2019, the contents of which are hereby incorporated by reference.

TECHNICAL FIELD

This disclosure relates to methods for treating cancer in a subject (e.g., an animal such as a human) in need thereof. In particular, the disclosure relates to methods for inducing malignant tumor regression.

BACKGROUND

Photodynamic therapy (PDT) is a technique useful for the treatment of cancer, in tumor-bearing organisms (e.g., animals including humans). PDT generally involves the systemic administration of a light-absorbing compound (i.e., a photosensitizer) to a tumor-bearing organism that sequesters within the tumor cell mass, followed by irradiation of the photosensitizer-laden tumor mass with light of an appropriate wavelength (i.e., in the therapeutic window of wavelengths between 600 to 700 nm, actinic light). This irradiation transfers energy to the photosensitizer in a manner that causes its conversion into a phototoxin (i.e., the excited state of the photosensitizer). The phototoxin is then able to chemically interact with surrounding molecules and alter them, e.g., via oxidation-reduction reactions or via the transfer of its energy to nearby oxygen, to generate singlet (excited state) oxygen. In turn, the singlet oxygen transfers its energy to surrounding molecules, damaging and/or degrading them. This damage from either of oxidation-reduction reactions or singlet oxygen energy transfer reactions impairs cellular organization and/or function, and thus reduces the viability of the (tumor) cell in which the phototoxin is present.

A particular class of photosensitizers, the benzophenoxazinium, benzophenothiazinium, and benzophenoselenazinium dyes, and their analogs/families/derivatives (collectively referred to as "BAs"), possess several properties that make them favorable for use as effective PDT photosensitizers. These properties include, e.g., a positive delocalized charge, high efficiency for absorbing light with a wavelength >600 nm (correlating with the light wavelengths in the "therapeutic window"), rapid absorption within a tumor cell mass, and ability to directly kill tumor cells (instead of only inflicting indirect damage, e.g., to the vasculature of and/or surrounding the tumor). See, e.g., Cincotta et al., *PhotoChem PhotoBiol* 46:751-758, 1987; Cincotta et al., *Cancer Res* 53:2571-2580, 1993; Cincotta et al., *Cancer Res* 54:1249-1258, 1994; U.S. Pat. Nos. 4,962,197; and 5,952,329 for further description of BAs-additional examples of BA dyes are described in U.S. Pat. No. 4,962,197, and all of the forgoing patents and references are hereby incorporated herein by reference in their entirety.

Further, BAs can undergo specific reactions within tumor cells and normal cells (including, e.g., different reactions within tumor versus normal cells) that influence their ability to absorb light in the therapeutic window. BAs can exist in, and reversibly transition between, an active cationic form (where they are able to absorb light in the therapeutic window and thus induce phototoxin production) and a neutral or reduced inactive form (where they are unable to absorb light in the therapeutic window). The main mechanisms involved in the inactivation of the BAs (rendering them unable to absorb light in the therapeutic window) are deprotonation based upon the pH of the environment (deprotonation in basic environment) and/or reduction of the BAs (particularly in the presence of a low oxygen concentration), induced for example by either cellular enzymatic processes, biochemical processes, and/or light (e.g., prolonged exposure to high-intensity light). The phototoxicity of the BAs also depends upon the intracellular location of the BAs, which is also a function of (and influences) their redox or protonation state. Therefore, the reactivity of the BAs to function as optimal PDT agents for cancer therapy depends upon their structure and chemical state within the tumor cell as well as the cellular biochemical environment within which they exist. For any given BA, a goal of PDT using these agents is to create a local intracellular environment that potentiates the appropriate level of photoactive (cationic) form of the BA at the time of photo-irradiation in a cellular location that most favorably facilitates cell killing and ultimate tumor eradication. This mechanism of BA-PDT directed tumor eradication may include and/or involve the appropriate stimulation of anti-tumor immune responses.

But tumor eradication with BA-PDT also involves more than just the direct photoactive reaction of light with the BA and resultant cell killing. Indeed, shortly following a PDT "event" (defined as irradiation of the tumor mass following the administration of one or more BAs), much of the tumor mass generally can remain intact and viable. However, during the ensuing days following the BA-PDT, the tumor mass can shrink and on certain occasions become completely resolved. This process involves the BA-PDT-initiated activation of a complex, innate and adaptive immune response against BA-PDT-treated tumor cells and, subsequently, tumor cells not directly affected by the BA-PDT. This immune-induced destruction of tumor cells is termed immunogenic cell death (See, e.g., Hendrzak-Henion et al., *PhotoChem PhotoBiol* 69:575-582, 1999).

While the direct effect of BA-PDT combined with its indirect, long-term immunogenic effect can produce reductions in tumor mass and may even result in tumor eradication in certain cases, the rate of such eradications (complete tumor response) has been and is generally both low and highly variable, both within a particular tumor type as well as between different tumor types. BA-PDT induced rates of eradication of immunogenic tumors can, e.g., vary from about 0% to about 40-60% within a given tumor type in a given species. Similarly, BA-PDT rates of eradication can vary between different tumor types in a given species, e.g., again generally from about 0% to about 40%. Rates of eradication of non-immunogenic tumors, although originally thought to be similar to that of immunogenic tumors, upon further investigation have been found to be generally much lower if at all however. This is a problem for effective treatment with BA-PDT in that many human tumor types are generally non-immunogenic, defined as a tumor type that does not elicit a strong immune response against the tumor that can potentially result in retardation or halt of tumor growth or tumor eradication. Responses to such BA-PDT treatments vary depending upon the method of presentation of the BA to the body (i.e., pharmacokinetics and pharmacodynamics) as well as the whole body and tumor metabolic status at the time of BA-PDT treatment.

Therefore, what is needed is a method providing a consistent and high eradication rate or similar successful tumor treatment rate (i.e., long-term remission post-treatment, long-term stasis post-treatment, reduced tumor growth rate post-treatment, or tumor free for a defined extended period of time post-treatment) for the treatment of tumors, particularly non-immunogenic tumors.

SUMMARY OF THE INVENTION

The present disclosure provides methods for treating cancer and/or inducing tumor regression in animals (e.g., humans) using metabolism-altering method(s) in conjunction with photodynamic therapy (e.g., PDT or BA-PDT)

The method includes the steps of increasing the metabolic activity level of a subject having a malignant tumor, and more specifically metabolic activity of the tumor which includes the host cells within the tumor mass. This tumor mass includes non-tumor cells. These non-tumor cells include fibroblasts, immunocytes, and other cell types within the subject. The metabolic activity of these cells is increased to a level above the basal metabolic activity level of the tumor or the subject, a BA dye is administered to the subject, and thereafter the tumor is exposed to actinic light for the BA dye. It is well established in the scientific and medical literature that providing metabolic substrates (human body fuel such as glucose, lipid, glutamine, amino acids) to an individual increases the metabolic activity of the individual and presentation of such materials to tumor cells of an individual increases their metabolic rate and enhances or promotes tumor growth, metastatic potential, and lethality and that excess consumption of high energy sugar or fat fuels should be avoided when combating cancer. Consequently, it is a general procedure to limit such fuels to the body and tumor to inhibit its growth rate. However, it has now surprisingly been found that the efficacy of BA-PDT therapy is significantly improved by increasing the metabolic activity level of a subject to a level above the subject's basal metabolic activity level prior to administration of BA-PDT therapy. The method disclosed herein is contrary to and the opposite of this well-established cause-effect relationship between increased level of fuel supply the body and the tumor, and the increased degree of tumor growth. Thus the disclosed method increases high energy fuel supply to the body, and the tumor (in conjunction with BA-PDT therapy) in order to inhibit (not promote) tumor growth.

In one embodiment the method includes the steps of increasing the metabolic activity level (e.g., rate of glucose, carbohydrate, lipid, amino acid, or protein production or utilization [anabolism or catabolism] that consumes or generates energy) of a subject having a malignant tumor to a level that is at least 10% above the basal metabolic activity level, administering a BA dye to the subject, and thereafter exposing the tumor to actinic light for the BA dye.

In another embodiment the method includes the steps of increasing the metabolic activity level (e.g., rate of glucose, carbohydrate, lipid, amino acid, or protein production or utilization) of the tumor of a subject having a malignant tumor to a level that is at least 10% above the basal metabolic activity level of the tumor of the subject, administering a BA dye to the subject, and thereafter exposing the tumor to actinic light for the BA dye.

In another embodiment the method includes the steps of raising the subject's plasma glucose and/or glutamine level by more than 10% above the subjects basal glucose and/or glutamine level, administering a BA dye to the subject, and thereafter exposing the tumor to actinic light for the BA dye.

In another embodiment the method includes the steps of raising the subject's plasma glucose and/or glutamine level and plasma insulin level by more than 10% above the subjects basal plasma glucose and/or glutamine level and plasma insulin level, administering a BA dye to the subject, and thereafter exposing the tumor to actinic light for the BA dye.

In another embodiment, the method includes the step of increasing the plasma glucose level of the subject by administering one or more hyperglycemic agents to the subject.

In another aspect, the method of treating a tumor includes the steps of increasing the plasma level of ketone, lactate, lipid, glutamine, and/or free fatty acid (FFA) of a subject in need of such treatment to a level above the basal ketone, lactate, lipid, glutamine, and/or free fatty acid (FFA) plasma level, respectively with or without increasing the plasma insulin level by at least 10% above basal level of the subject, administering at least one BA to the subject, and thereafter exposing the tumor to actinic light for the BA.

In another embodiment, the method includes the steps of administering BA dyes to a subject, comprising intravenously infusing into the subject a BA solution in a volume equal to between about one-tenth and one-third of the total blood volume of the subject at a rate that creates a plasma BA $T_{max}$ within about 360 minutes, preferably 240 minutes following termination of infusion, and a plasma level of less than about 50% of the $T_{max}$ level between about 30-360 minutes, preferably about 30-240 minutes following the $T_{max}$ time.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description, and from the claims.

DETAILED DESCRIPTION

Figure 1:
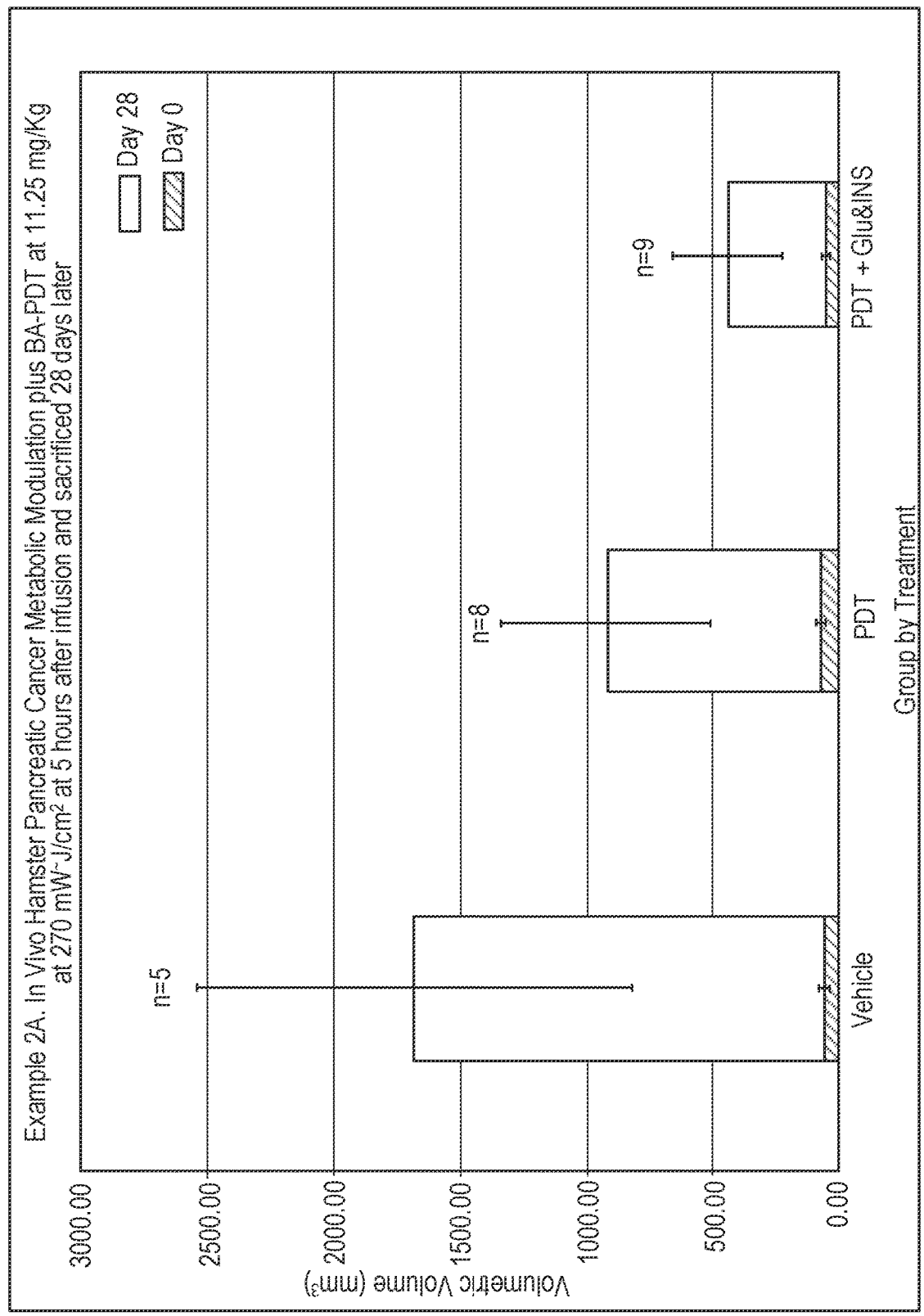
FIG. 1 is a chart illustrating the in vivo anti-tumor effect of Hamster Pancreatic Cancer Metabolic Modulation plus BA-PDT at 11.25 mg/kg at 270 mW~J/cm² at 5 hours after BA infusion and sacrificed 28 days later.

As used herein, the terms "about" and "approximately" are defined as being within plus or minus (±) 10% of a given value or state, preferably within ±5% of said value or state.

The terms "tumor", "tumor mass, and "solid tumor," as used herein, refer to an abnormal tissue growth or mass (i.e., a neoplasm) comprising cells having one or more mutations and supportive cells (e.g., non-cancerous stromal cells surrounding the mutated cancer cells). Tumors can be, e.g., benign, in situ, and/or malignant. A "cancer," as used herein, refers to one or more malignant tumors. Tumor types treatable by the current invention include tumors of endodermal, mesodermal, and ectodermal tissue origins and a non-limiting list of treatable tumors includes tumors of the brain, colon, breast, pancreas, lung, prostate, muscle, liver, lymphomas, and blood (e.g., leukemias).

The term "basal level" as used herein refers to the stable concentration of a test substance following an overnight fast of the test substance e.g. glucose, glutamate, insulin, or other humoral factors, in the subject's plasma or measures of subject or tumor metabolic rate or activity prior to treatment with the methods disclosed herein.

The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of cancer).

It has now surprisingly been found that the tumor eradication rate/treatment efficacy of PDT can be significantly enhanced/increased by combining PDT (e.g., BA-PDT) with one or more metabolism-altering techniques (i.e., methods that alter the metabolic state (increase metabolic activity) of the tumor mass and optionally increase the metabolic activity of distant normal tissue (e.g. increasing the subject's metabolic activity) as described herein below. When co-administered with PDT, the metabolism-altering methods disclosed herein increase both the phototoxic and the immunogenic effectiveness of the BA-PDT (MetabBA-PDT) and increases the anti-tumor effect. The method can be used to treat mammals (including, e.g., animals and humans) in need of tumor treatment (reduction in or eradication of tumor mass).

The method comprises increasing the subject's whole body metabolic activity and/or tumor growth promoting metabolism (increasing, e.g., whole body or tumor glycolysis, mitochondrial oxidative phosphorylation, and/or energy production and/or utilization for subsequent anabolic and/or catabolic processes) by any of a variety of methods including increasing the metabolic fuel supply to the body and/or tumor, followed by administration of BA-PDT. This is a unique, counterintuitive approach to tumor/cancer treatment and eradication inasmuch as one skilled in the art would be disposed against increasing metabolic activity in cancer cells with nutrients that are well established to support their growth as a means of destroying such cells. In fact, a general practice in oncology is to alter the nutrition of the subject in a manner to reduce the sugar and lipid content of the diet in order to reduce tumor metabolism and thereby retard tumor growth (i.e., to starve the tumor). Conversely, however, in the context of the present treatment, an increase in tumor (cancer cell and surrounding normal stromal cell microenvironment) metabolic activity potentiates the effectiveness of the subsequent BA-PDT to produce an interactive and robust destruction of tumor tissue (i.e., a potent anti-tumor response). Increasing the metabolic activity of the or tumor (with or without increasing the metabolic activity of the body), when combined with BA-PDT, allows for an enhanced antitumor therapeutic effect.

For example, the method comprises increasing the subject's basal plasma glucose and/or glutamine level by any means (e.g., by at least 10, 15, 20, 25, 30, 35, 40, 45, or 50%) above the basal level for a period of time, followed by administering BA-PDT treatment to the subject (hereinafter the Glu-BA-PDT method). Moreover, the increased plasma glucose and/or glutamine level can be present prior to, or concurrent with, the administration of one or more BAs or after the administration of one or more BAs and can extend up to (i.e., be sustained at least until) a PDT event (photoirradiation) comprising exposure to an actinic light source (which is generally administered at a time between 30 minutes to 24 hours after BA administration). The time period during which the subject's plasma glucose or glutamine level is increased over the subject's basal level of these constituents can start before administration of the BAs (for example within 24 hours before) or later (i.e., after the BA has been administered but before photoirradiation) and/or extend later (i.e., after photoirradiation). For example, the subject's plasma glucose or glutamine level can be increased over the basal level of such constituents by any means (e.g., increased by at least 10, 15, 20, 25, 30, 35, 40, 45, or 50% above the basal level) starting at any time point beginning at least at about 180 minutes before the administration of one or more BAs and extending to the time of photoirradiation. For example, in one embodiment, the increased plasma glucose or glutamine level can extend at least to (i.e., be sustained at least until) 180 minutes after the PDT event (exposure of the tumor to actinic light). For example, in some embodiments, the subject's plasma glucose or glutamine level can be increased by any means (e.g., by at least 10, 15, 20, 25, 30, 35, 40, 45, or 50%) above the basal level starting seven days before the administration of one or more BAs and extending to (i.e., maintained at the increased level until) 48 hours after photoirradiation. In other words, the window in which the plasma glucose or glutamine level increase should be initiated begins about 7 days prior to administration of the BA and extends until about 10 minutes prior to photoirradiation and such increased level is maintained at least until photoirradiation. Preferably, the subject's plasma glucose and/or glutamine level can be increased for a time period beginning between about 24 hours before BA administration or photoirradiation and the increased metabolic level maintained until at least the time of photoirradiation, and optionally maintained for some time thereafter, e.g. up to 24 hours after photoirradiation.

Alternately or in addition, the method comprises increasing the plasma lactate, ketone (e.g., alpha ketobutyrate), lipid, and/or free fatty acid (FFA) level of the subject by any means (e.g., by at least 10, 15, 20, 25, 30, 35, 40, 45, or 50%) above the basal level for a period of time followed by administering BA-PDT to the subject (hereinafter the FFA-BA-PDT method). Moreover, the increased the plasma lactate, ketone (e.g., alpha ketobutyrate), lipid, and/or free fatty acid (FFA) level can be initiated prior to, or concurrent with the administration of one or more BAs or after the administration of one or more BAs, and can extend up to (i.e., be sustained at least until) a PDT event comprising exposure to an actinic light source (which is generally administered at a time between 30 minutes to 24 hours after BA administration). The time period during which the subject's plasma lactate, ketone (e.g., alpha ketobutyrate), lipid, and/or free fatty acid (FFA) level is increased over the subject's basal level of these constituents can start much earlier before the administration of the BAs (for example within 24 hours before) or later (i.e., after the BA has been administered but before photoirradiation) and/or extend later (i.e., after photoirradiation). For example, in one embodiment, the subject's plasma lactate, ketone (e.g., alpha ketobutyrate), lipid, and/or free fatty acid (FFA) level can be increased over the basal level of such constituents by any means (e.g., increased by at least 10, 15, 20, 25, 30, 35, 40, 45, or 50%) above the basal level starting at any time point beginning at least 120 minutes, and up to 24 hours, before the administration of one or more BAs and such starting point extending up to 30 minutes before the time of photoirradiation. For example, in some embodiments, the increased plasma lactate, ketone (e.g., alpha ketobutyrate), lipid, and/or free fatty acid (FFA) level can extend at least to (i.e., be sustained at least until) 180 minutes after the PDT event (exposure of the tumor to actinic light). For example, the subject's plasma lactate, ketone (e.g., alpha ketobutyrate), lipid, and/or free fatty acid (FFA) level can be increased by any means (e.g., by at least 10, 15, 20, 25, 30, 35, 40, 45, or 50%) above the basal level starting within seven days before the administration of one or more BAs and extending the increased level (i.e., maintained at the increased level until) for as long as up and optionally 48 hours after the PDT event (photoirradiation). In other words, the window in which the plasma lactate, lipid or FFA level increase should be initiated begins about 7 days prior to administration of the BA and extends until about 10 minutes prior to photoirradiation and such increased levels should be maintained until at least photoirradiation. Preferably, the subject's plasma lactate, ketone (e.g., alpha ketobutyrate), lipid, and/or free fatty acid (FFA) level can be increased for a time period beginning between about 24 hours before BA administration and at least 10 minutes before the time of irradiation and optionally maintained at least until the photoirradiation.

Alternately or in addition, the method comprises increasing plasma insulin (e.g., by at least 10, 15, 20, 25, 30, 35, 40, 45, or 50%) above the subjects basal plasma insulin level for a period of time (hereinafter the "enhanced activity period") followed by BA-PDT treatment (I-BA-PDT). Moreover, the enhanced activity period can be initiated prior to or concurrent with the administration of one or more BAs or after the administration of one or more BAs and can extend up to (i.e., be sustained at least until) a PDT event comprising exposure to an actinic light source (which is generally administered at a time between 30 minutes to 24 hours after BA administration). The time period during which the subject's plasma insulin level is increased over the subject's basal level of these constituents can start much earlier before the administration of the BAs (for example within 12 hours before) or later (i.e., after the BA has been administered but before photoirradiation) and/or extend later (i.e., after photoirradiation). For example, in one embodiment, the subject's plasma insulin level can be increased above the basal level by any means (e.g., increased by at least 10, 15, 20, 25, 30, 35, 40, 45, or 50%) starting at any time point beginning at least 30 minutes before the administration of one or more BAs and extending to the time of photoirradiation. For example, the increased plasma insulin level can extend at least to (i.e., be sustained at least until) 180 minutes after the PDT event (exposure of the tumor to actinic light). For example, the subject's plasma insulin level can be increased by any means (e.g., by at least 10, 15, 20, 25, 30, 35, 40, 45, or 50%) above the basal level starting 12 hours before the administration of one or more BAs and extending to (i.e., maintained at the increased level until) 180 minutes after the PDT event. Preferably, the subject's plasma insulin level can be increased beginning at any time point between about seven days (preferably 24 hours) before BA administration and 10 minutes before the time of irradiation. In other words, the window in which the plasma insulin level increase should be initiated begins about 7 days prior to administration of the BA and extends until about 10 minutes prior to photoirradiation and such plasma insulin level increase should be maintained until at least the time of photoirradiation. Similarly, any method that initiates the increased metabolic, glycolytic or mitochondrial activity of the subject or tumor beginning from 7 days (preferably 24 hours) before the administration of BA and extending until about 10 minutes before the BA-PDT irradiation will enhance the BA-PDT effectiveness in destroying the tumor. In other words, the window in which the metabolic activity increase should be initiated begins about 7 days prior to administration of the BA and extends until about 10 minutes prior to photoirradiation and such increased metabolic, glycolytic or mitochondrial activity should be maintained until at least the time of photoirradiation. A variety of other agents beyond those described above that enhance metabolic, glycolytic, or mitochondrial oxidative activity of the tumor will also function to enhance the BA-PDT effectiveness in destroying the tumor. These agents include, by way of non-limiting example, stimulators of UCP1,2, or 3 (norepinephrine, epinephrine) or uncouplers of oxidative phosphorylation such as dinitorphenol, FCCP (Carbonyl cyanide-4-(trifluoromethoxy)phenylhydrazone), oligomycin, pyruvate dehydrogenase stimulators (e.g., insulin, carnitine) and thyroid hormones (T3,T4). Whole body glycolytic activity, lipid oxidation activity, and metabolic rate can be measured by any means known in the art including respirometry assessment of O2 consumption and CO2 production. Tumor oxidative or metabolic activity can be measured with the use of stable or radiolabeled isotopes to measure local glucose uptake, oxygen consumption, or CO2 production.

It is desirable to wait about 30 minutes to about 8 hours between the time the subject's metabolic profile has reached the desired "increased" level (i.e., the level above the basal level of e.g. plasma glucose, FFA, lipid, ketone, lactate, or glutamine) and administration of the BA dye. However, longer periods of increased metabolic activity in the subject or tumor for as long as one week may also be useful in this treatment paradigm. However, such "increased" metabolic activity level can also be established within 24 hours prior to the BA administration and up to about 30 minutes prior to photoirradiation of the tumor. This increase can begin after the administration of the BAs and before BA-PDT photoirradiation.

Any of the above methods of increasing the subject's metabolic activity (e.g., glycolytic activity, lipid oxidation activity, oxygen consumption rate, fuel utilization rate, anabolic and/or catabolic processes) can be applied individually or in any combination prior to the administration of one or more BA dyes. For example, the GluBA-PDT method can be combined with the FFA-BA-PDT method to further enhance tumor eradication (defined as the MetabBA-PDT method). In another example, the GluBA-PDT, FFA-BA-PDT, or MetabBA-PDT method can further be combined with increasing plasma insulin (e.g., by at least 10, 15, 20, 25, 30, 35, 40, 45, or 50%) above the basal level for a period of time as defined above.

An increase in plasma glucose and/or glutamine level (e.g., by at least 10, 15, 20, 25, 30, 35, 40, 45, or 50%) above the basal level for a period of time can be achieved by any means or combination of means known in the art, including, e.g., a) direct glucose and/or glutamine administration to achieve a prolonged hyperglycemia and/or elevated plasma glutamine levels (e.g., administration of a glucose and/or glutamine bolus, intravenous glucose and/or glutamine, or a glucose and/or glutamine bolus followed by continuous intravenous glucose and/or glutamine), b) administration of one or more hormones or hyperglycemic agents (e.g., glucagon, corticosteroids, and growth hormone) to increase plasma glucose level, c) administration of one or more xenobiotics that elevate the plasma glucose level, and/or d) any nutritional (e.g., dietary), pharmaceutical, and/or biological intervention that produces a sustained rise in the plasma glucose level (e.g., consuming high glycemic index food such as a candy bar, pastry, potato or a sugar containing beverage).

An increase in plasma lactate, ketone, lipid, and/or FFA level (e.g., by at least 10, 15, 20, 25, 30, 35, 40, 45, or 50%) above the basal level for a period of time can be achieved by any means or combination of means known in the art, including, e.g., a) direct lactate, ketone, lipid, and/or FFA administration (e.g., lipid or fat emulsion [e.g., Intralipid® infusion]), and/or b) administration of one or more lipolytic agents (e.g., growth hormone, corticosteroids, thyroid hormones, and/or acipomox) and/or sympathomimetic agents (e.g., agents that increase noradrenergic or adrenergic activity at adipocytes such as, e.g., norepinephrine, epinephrine, beta-3 agonists, and/or noradrenergic alpha 1 and/or 2 agonists) that facilitate a rise in plasma FFA level.

An increase in plasma insulin (e.g., by at least 10, 15, 20, 25, 30, 35, 40, 45, or 50%) above the basal level for a period of time can be achieved by any means or combination of means known in the art, including, e.g., insulin infusion, insulin injection, and/or FFA infusion or consumption of a high sugar (for example greater than 75 grams per serving of sugar) or carbohydrate diet, a high fat diet (greater than 25% of total daily calories from fat), or a high fat plus simple sugar diet An increase in plasma corticosteroid level (e.g., by at least 2-fold) above the basal level for a period of time can be achieved by any means or combination of means known in the art, including, e.g., corticosteroid infusion or injection or oral administration.

Any of the above described methods of increasing metabolic activity of the body can function to increase the metabolic activity of the normal tissue within (and potentially surrounding) the tumor mass that, in turn, functions to increase lactate and ketone production and release that enters the tumor mass to increase its metabolic activity, thereby increasing the effectiveness of the BA-PDT. As such, the normal tissue can participate in a major way in the destruction of the tumor mass with this unique anti-cancer treatment approach.

A preferred BA chromophore for use in the present tumor eradication treatment is a benzophenothiazinium compound, an iodinated benzophenoxazinium compound, or a pharmaceutically acceptable salt thereof. In a particularly preferred embodiment, the BA chromophore is 2-iodo-5-ethylamino-9-diethylamino-benzo[a]phenothiazinium chloride (2I-EtNBS), 5-ethylamino-9-diethylamino-benzo[a]phenothiazinium chloride (EtNBS), or 5-ethylamino-9-diethylaminobenzo[a]phenoselenazinium (EtNBSe). The amount of BA for each treatment ranges between 0.01 to 15 mg/kg. The BAs are generally dissolved in an acidic aqueous solution of 3-10% simple sugar (glucose, sucrose, etc.). The BAs are administered at a predetermined intravenous infusion rate to provide for a specific pharmacokinetic profile. Generally, the intravenous infusion of the BA dye solution is at a rate that creates a plasma BA $T_{max}$ of the BA within about 10-240 minutes, preferably within about 10-180 minutes, following termination of infusion, followed by a plasma level of the BA less than about 50% of the $T_{max}$ level within about 30 to 360 minutes, preferably within about 30 to 240 minutes following the initial $T_{max}$ time.

An optimal outcome of a successful cancer therapy (e.g., successful BA-PDT therapy) is a therapeutically relevant and maximal level of damage to the tumor, combined with a minimal level of damage to the healthy/normal body tissues of the subject.

The optimal therapeutic effect of BA-PDT therapy is dependent upon a complex interaction of pharmacodynamic, photophysical, and biochemical events within the subject. To optimize the therapeutic benefit and provide a maximal therapeutic index (defined as the minimal dose that produces a toxic effect to the body divided by the minimum effective therapeutic dose of the therapy) on a routine, reproducible basis with BA-PDT, a specific method of administering the BA is employed based upon the following considerations.

BA chromophores (BAs) are taken up by both normal and tumor/cancer cells; however, they tend to be retained within tumor/cancer cells of the body for a longer period of time than within normal cells. BA chromophores can be toxic to normal tissues, even in the absence of light. Also, within both normal cells and tumor/cancer cells, BA dyes (BAs) can exist in an active oxidized or protonated form and/or an inactive reduced or deprotonated form. To increase the therapeutic benefit and therapeutic index simultaneously with BA-PDT, it is advantageous to maximize the amount of oxidized or protonated BA dyes in cancer cells while limiting the level of such oxidized or protonated dyes in normal cells. This is because it is the oxidized or protonated form of the BA dyes that effectively absorb light in the therapeutic window to produce the PDT anti-cancer effect.

To generate a PDT effect with BA dyes, previous studies have employed either an intravenous injection, subcutaneous injection, or intravenous infusion of the BA dye at a standard rate and volume (irrespective of subject blood volume, i.e., dosing not based the subject's blood volume) with varying therapeutic effect.

BA dyes can be rapidly cleared from the circulation and absorbed by both healthy/normal and cancerous tissues of the body shortly after administration depending upon the administration protocol. Also, BA dyes can be rapidly inactivated (i.e., converted to a form that does not absorb light at the appropriate wavelength and therefore is non-photoactive) in both healthy/normal and cancerous tissues. Thus, to enable an administered dose of BA dye to 1) differentially and preferentially accumulate within cancerous tissues versus healthy/normal tissues of the body, 2) maximally remain in the active form at the time of tumor irradiation, and 3) maintain a beneficial maximal therapeutic index, the administration volume, rate, and dose of BA dye must be appropriately adjusted.

Unlike most pharmacological agents, the absorption, distribution, metabolism, and elimination (ADME) of the BA dyes interacts with their photophysical properties to determine their therapeutic index. Importantly, it has now been found that BA dyes' ADME can be manipulated in a very specific way to optimize their therapeutic effect at the same dose administration by employing a specific procedure for the administration and irradiation of the BA dyes. In particular, it has now been unexpectedly found that a specific administration and irradiation procedure for BA dyes is required to achieve a superior BA-PDT result and physiological status with healthy/normal tissues containing low (i.e., non-toxic) levels of BA dyes (low levels of oxidized or protonated BA dyes in particular) and cancerous tissues containing a relatively higher level of oxidized or protonated BA dyes (i.e., a level sufficient to produce a therapeutically relevant PDT effect on tumor growth and viability [optimal BA-PDT procedure]). That is to say, specific administration procedures and light treatment procedures produce an unexpectedly superior PDT result versus other procedures that utilize the same dose of BA and light. This procedure has the following components and characteristics:

1. Administration (by intravenous infusion) of a BA dose between about 0.01 to 15 mg/kg body weight (preferably about 0.01 to 5.0 mg/kg body weight) in an acidified aqueous solution of 3-10% sugar or any short chain saccharide(s) (e.g., glucose, sucrose, mannitol, mannose, and/or fructose).
2. Intravenous infusion of the BA dye solution at a total infusion volume equal to between about one-tenth and one-quarter of the subject's total blood volume.
3. Intravenous infusion of the BA dye solution at a rate that creates a plasma BA $T_{max}$ within about 10-240 minutes, preferably within about 10-180 minutes following termination of infusion, followed by a plasma level less than about 50% of the $T_{max}$ level within about 10 to 360 minutes, preferably within about 30 to 240 minutes following the initial $T_{max}$ time.
4. Irradiation of the tumor mass within about 30 minutes to 24 hours, preferably to 8 hours following the termination of BA dye infusion with "red" light (i.e., light with a wavelength between about 600 and 700 nm, preferably >650 nm, preferably at the lambda max for the specific BA dye administered) at 50-500 mW/cm$^2$ and 50-500 J/cm$^2$.

Light Activation of Administered BA Chromophores

Light-induced killing of solid tumors can be carried out on any solid tumor accessible to irradiation from conventional sources of actinic light (e.g., a xenon arc lamp or an incandescent white light source) and/or from a laser generating light of the appropriate wavelength [i.e., at or near the lambda max absorption of the BA]. For tumors on the body surface, any light source can be employed that radiates light at the appropriate wavelengths to activate the BA chromophores (i.e., wavelengths between about 600 and 700 nm, preferably between about 620 and 700 nm, preferably about 650 nm) and that can deliver about 50 to 500 mW per square centimeter (cm$^2$) of treated area. For example, a diode laser or a tunable argon-dye laser (e.g., a 5 watt argon ion pumped tunable dye laser such as Coherent model Innova 100) can be used. Similar lasers are also commercially available from, e.g., Applied Optics Corp. (e.g., a 652 nm diode laser). A projector light source can alternately be employed. For tumors within the body that are inaccessible to direct light sources, light can be administered, e.g., via optical fibers. A preferred light source in this case is a laser.

The total light energy delivered is preferably between about 50 and about 500 Joules (J)/cm$^2$, more preferably about 200 J/cm$^2$. The power density of the light is preferably between about 50 and about 500 mW/cm$^2$, more preferably about 200 mW/cm$^2$. Delivery of laser light can be carried out, e.g., according to the well-known methods currently used for HPD-mediated laser therapy (see, e.g., Foultier et al., *J Photochem Photobiol B Biol.* 10:119-132, 1991). The output beam from the dye laser can be coupled to, e.g., a 400 micron (μm) quartz fiber optic cable fitted with a microlens to ensure an even light distribution throughout the treatment field. The wavelength can be tuned with, e.g., a birefringent filter and the power density should be adjusted for a spot size to encompass the tumor and a margin of some normal tissue.

Compared to BA-PDT alone, the application of one or more metabolism-altering methods as described herein in conjunction with BA-PDT (e.g., GluBA-PDT or FFA-BA-PDT or MetabBA-PDT) leads to a surprising and apparently synergistic enhancement of the tumor eradication rate, with one or more of the metabolism-altering methods disclosed herein.

Assessment of the change in metabolism in the tumor desired to be treated by any of the metabolism-altering methods described herein may be accomplished by altering the metabolism as described herein of the tumor type desired to be treated (e.g., increasing the tumor level of glucose, glutamine, lactate, ketone, lipid, and/or FFA [e.g., by at least 10, 15, 20, 25, 30, 35, 40, 45, or 50%] above that of the subject's basal condition for a period of time) and evaluating subsequent changes in metabolic activity of the tumor, for example, by assaying activity levels of glucose uptake, glycolysis, mitochondrial oxidative phosphorylation, and/or reactive oxygen species generation by methods that are well established in the art. The increase in the photoactive form of the BA within the tumor or tumor cells under such metabolic manipulation conditions can be evaluated in vivo. This measurement can be accomplished using spectrophotometry (red light absorption) or fluorescence analysis of BA's within the tumor mass.

EXAMPLES

Example 1

Syrian hamsters bearing transplanted subcutaneous pancreatic tumors (~5-9 mm diameter) (HapT1, from approximately 1 million cells injected) were divided into three groups (N=3-6 per group). Two groups were administered BA (2I-EtNBS) (6.0 mg/kg), either with concurrent intervention to raise the plasma glucose level (glucose bolus administration [3 g/kg body weight, administered intraperitoneally]) to at least 20% above basal levels (Glu-BA-PDT) plus insulin (10 U/kg body weight) for a period from 30 minutes prior to BA administration to 60 minutes after BA administration or another group without such metabolic treatment. A third group was untreated to serve as a negative control. Each of the BA groups received PDT (180 mW/cm$^2$ and 180 J/cm$^2$ of 652 nm light) 60 minutes after the administration of BA. Relative to the untreated control group, the tumor volume at 3-7 days following PDT was reduced by 40-50% in the BA-PDT group and by 70-80% in the Glu-BA-PDT plus insulin group. In other words, the tumor growth promoting intervention of adding the glucose plus insulin to the BA-PDT protocol further reduced tumor growth by another approximate 50%.

Example 2A

Syrian hamsters bearing transplanted orthotopic pancreatic tumors (~5-9 mm diameter) (HapT1, from approximately 100,00 cells injected) were divided into three groups (N=5-9/group). Two groups were administered BA (2I-EtNBS) (11.25 mg/kg), either with prior intervention to raise the plasma glucose level (glucose bolus administration [3 g/kg body weight, administered intraperitoneally]) to at least 20% above basal levels (Glu-BA-PDT) plus insulin (10 U/kg body weight) for a period from 60 minutes prior to BA-PDT photoirradiation and 4 hours after BA administration or another group without such metabolic treatment. A third group was untreated to serve as a negative control. Each of the BA groups received PDT (270 mW/cm² and 270 J/cm² of 652 nm light) 5 hours after the administration of BA. Tumor growth was assessed by measuring tumor volume at 28 days post-BA-PDT treatment. Relative to the untreated control group (tumor volume=1686 mm³), the tumor volume of the BA-PDT group was approximately 45% smaller. However, the tumor volume of the BA-PDT plus glucose and insulin group was 52% smaller than the BA-PDT group. In other words, the tumor growth promoting intervention of adding the glucose plus insulin to the BA-PDT protocol further reduced tumor growth by another 38%.

FIG. 1 is a chart of Example 2A illustrating the in vivo anti-tumor effect of Hamster Pancreatic Cancer Metabolic Modulation plus BA-PDT at 11.25 mg/kg at 270 mW~J/cm² at 5 hours after infusion treatment and sacrificed 28 days later.

The results of Example 2A are shown below—values are for tumor volume in mm³.

| Vehicle tumor volume (mm3) | | | PDT tumor volume (mm3) | | | PDT + Glu&INS minor volume (mm3) | | |
|---|---|---|---|---|---|---|---|---|
| Hamster # | Day 0 | Day 28 | Hamster # | Day 0 | Day 28 | Hamster # | Day 0 | Day 28 |
| 1072518 | 52.91 | 0.00 | 2072018 | 25.98 | 363.55 | 3072018 | 22.01 | 0.00 |
| 13072518 | 27.04 | 4137.31 | 4072018 | 28.46 | 0.00 | 5072018 | 34.63 | 0.00 |
| 1072018 | 41.33 | 3214.92 | 6072018 | 51.14 | 0.00 | 7072018 | 60.50 | 0.00 |
| 12072018 | 54.68 | 0.00 | 8072018 | 170.55 | 1128.59 | 9072018 | 34.96 | 97.55 |
| 13072018 | 105.34 | 1079.03 | 10072018 | 55.12 | 152.49 | 11072018 | 61.66 | 0.00 |
| | | | 6072718 | 74.92 | 836.34 | 2072718 | 83.05 | 0.00 |
| | | | 9072718 | 69.55 | 3512.44 | 5072718 | 46.08 | 1483.99 |
| | | | 12072718 | 59.40 | 1395.92 | 8072718 | 44.57 | 1356.32 |
| | | | | | | 11072718 | 32.07 | 1034.39 |
| Average | 56.26 | 1686.25 | Average | 66.89 | 923.67 | Average | 46.61 | 441.36 |

Example 2B

Syrian hamsters bearing transplanted orthotopic pancreatic tumors (~5-9 mm diameter) (HapT1, from approximately 100,00 cells injected) were divided into three groups (N=7-15/group). Two groups were administered BA (2I-EtNBS) (11.25 mg/kg), either with prior intervention to raise the plasma glucose level (glucose bolus administration [3 g/kg body weight, administered intraperitoneally]) to at least 20% above basal levels (Glu-BA-PDT) plus insulin (10 U/kg body weight) for a period from 60 minutes prior to BA-PDT photoirradiation and 4 hours after BA administration or another group without such metabolic treatment. A third group was untreated to serve as a negative control. Each of the BA groups received PDT (270 mW/cm² and 270 J/cm² of 652 nm light) 5 hours after the administration of BA. Tumor growth was assessed by measuring tumor volume at 7 days post-BA-PDT treatment. Relative to the untreated control group (tumor volume=597 mm³), the tumor volume of the BA-PDT group was approximately 41% smaller. However, the tumor volume of the BA-PDT plus glucose and insulin group was 63% smaller than the BA-PDT group. In other words, the tumor growth promoting intervention of adding the glucose plus insulin to the BA-PDT protocol further reduced tumor growth by another 63%.

Figure 2:
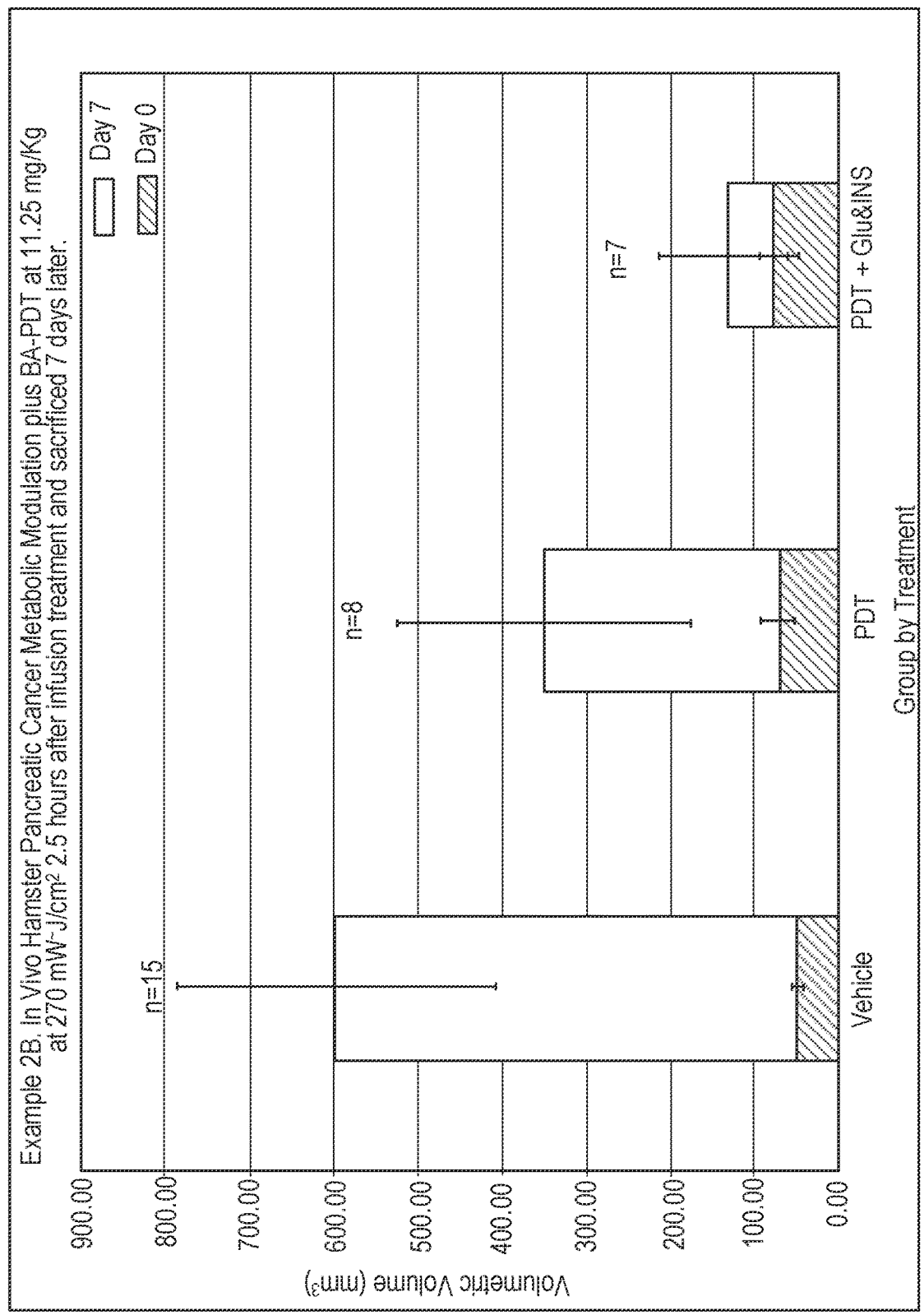
FIG. 2 is a chart illustrating the anti-tumor effect of in vivo Hamster Pancreatic Cancer Metabolic Modulation plus BA-PDT at 11.25 mg/kg at 270 mW~J/cm² at 2.5 hours after BA infusion treatment and sacrificed 7 days late

FIG. 2 a chart of Example 2B illustrating the in vivo Hamster Pancreatic Cancer Metabolic Modulation plus BA-PDT at 11.25 mg/kg at 270 mW~J/cm² 2.5 hours after infusion treatment and sacrificed 7 days later, The results of Example 2B are shown below—values are for tumor volume in mm³.

| Vehicle tumor volume mm³ | | | PDT tumor volume (mm3) | | | PDT + Glu&INS tumor volume (mm3) | | |
|---|---|---|---|---|---|---|---|---|
| Hamster # | Day 0 | Day 7 | Hamster # | Day 0 | Day 7 | Hamster # | Day 0 | 7 |
| 1071818 | 34.05 | 2368.50 | 3071818 | 76.23 | 0.00 | 2071818 | 169.53 | 68.47 |
| 12071818 | 53.59 | 2346.63 | 5071818 | | 684.16 | 4071818 | 44.80 | 0.00 |
| 12060418 | 67.03 | 404.31 | 7071818 | 50.25 | 1355.70 | 6071818 | 59.96 | 138.12 |

-continued

| Vehicle tumor volume mm³ | | | PDT tumor volume (mm3) | | | PDT + Glu&INS tumor volume (mm3) | | |
|---|---|---|---|---|---|---|---|---|
| Hamster # | Day 0 | Day 7 | Hamster # | Day 0 | Day 7 | Hamster # | Day 0 | 7 |
| 12053118 | 44.40 | 343.28 | 9071818 | 189.45 | 0.00 | 8071818 | 86.36 | 628.62 |
| 1052918 | 28.75 | 233.98 | 11071818 | 66.32 | 426.06 | 10071818 | 50.62 | 0.00 |
| 1052518 | 23.50 | 385.64 | 6060418 | 36.06 | 108.47 | 2060418 | 76.40 | 20.16 |
| 12051818 | 59.83 | 79.72 | 8060418 | 51.96 | 102.76 | 7060418 | 50.64 | 59.70 |
| 8042118 | 83.44 | 240.35 | 10060418 | 29.70 | 141.74 | | | |
| 1041918 | 46.70 | 526.84 | | | | | | |
| 13071818 | 77.90 | 240.35 | | | | | | |
| 4060418 | 69.14 | 526.84 | | | | | | |
| 1053118 | 49.53 | 526.99 | | | | | | |
| 12052918 | 61.34 | 491.81 | | | | | | |
| 12052518 | 23.80 | 139.83 | | | | | | |
| 1051818 | 35.34 | 107.14 | | | | | | |
| Average | 50.56 | 597.48 | Average | 71.42 | 352.36 | Average | 76.90 | 130.72 |

Example 3

Syrian hamsters bearing transplanted subcutaneous pancreatic tumors (~5-9 mm diameter) (HapT1, from approximately 1 million cells injected) were divided into three groups. Two groups were administered 2I-EtNBS (BA) (6.0 mg/kg), either with concurrent intervention to raise the plasma FFA and glucose levels (e.g., administration of a lipid/fat emulsion as Intralipid® at about 7.5 ml of a 20% solution per kg body weight and of glucose at 3 g/kg body weight i.p.) to at least 30% above basal levels for a period from 60 minutes prior to BA administration to about 60 minutes after BA administration (Metab-BA-PDT) plus insulin (10 U/kg body weight) or another group without such treatment (BA-PDT). A third group was untreated to serve as a negative control. Each of the BA groups receive PDT (180 mW/cm² and 180 J/cm² of 652 nm light) 60 minutes after the administration of BA. Relative to the untreated control group, the tumor volume at 4-7 days following PDT was reduced by 40-50% in the BA-PDT group and by 70-80% in the Metab-BA-PDT plus insulin group. In other words, the tumor growth promoting intervention of adding the glucose plus insulin to the BA-PDT protocol further reduced tumor growth by another approximate 50%.

Example 4

Syrian hamsters bearing transplanted subcutaneous pancreatic tumors (~5-9 mm diameter) (HapT1, from approximately 1 million cells injected) were divided into three groups. Two groups are administered 2I-EtNBS (BA) (6.0 mg/kg), either with concurrent intervention to raise the plasma FFA (e.g., administration of a lipid/fat emulsion as Intralipid® at about 7.5 ml of a 20% solution per kg body weight) to at least 30% above basal levels for a period from 60 minutes prior to BA administration to about 60 minutes after BA administration (FFA-BA-PDT) or another group without such intervention (BA-PDT). A third group is untreated to serve as a negative control. Each of the BA groups receive PDT (180 mW/cm² and 180 J/cm² of 652 nm light) 60 minutes after the administration of BA. Relative to the untreated control group, the tumor volume at 4-7 days following PDT was reduced by 40-50% in the BA-PDT group and by 70-80% in the FFA-BA-PDT group. In other words, the tumor growth promoting intervention of adding the glucose plus insulin to the BA-PDT protocol further reduced tumor growth by another approximate 50%.

Example 5

Syrian hamsters bearing transplanted subcutaneous pancreatic tumors (~5-9 mm diameter) (HapT1, from approximately 1 million cells injected) are divided into three groups. Two groups are administered 2I-EtNBS (BA) (6.0 mg/kg), either with (FFA-BA-PDT) or another group without (BA-PDT) concurrent intervention to raise the plasma lactate and/or ketone level to at least 10% above basal levels for a period from 30 minutes prior to BA administration to 60 minutes after BA administration. A third group is untreated to serve as a negative control. Each of the BA groups receive PDT (exposure to 180 mW/cm² and 180 J/cm² of 652 nm light) 60 minutes after the administration of BA. Relative to the BA-PDT group, the decrease in tumor size in the FFA-BA-PDT group at 4-7 days post-PDT is predicted to be significantly greater than in the control and BA-PDT groups.

Example 6

Syrian hamsters bearing transplanted subcutaneous pancreatic tumors (~5-9 mm diameter) (HapT1, from approximately 1 million cells injected) were divided into three groups. Two groups were administered 2I-EtNBS (BA) (6.0 mg/kg), either with concurrent intervention to raise the plasma glucose level to at least 30% above basal levels for a period from about 60 minutes prior to BA administration to 60 minutes after BA administration (Glu-BA-PDT) or another group without such intervention (BA-PDT). A third group was untreated to serve as a negative control. Each of the BA groups received PDT (180 mW/cm² and 180 J/cm² of 652 nm light) 60 minutes after the administration of BA. Relative to the untreated control group, the tumor volume at 3-7 days following PDT was reduced by 30-50% in the BA-PDT group and by 70-80% in the Glu-BA-PDT. In other words, the tumor growth promoting intervention of adding the glucose to the BA-PDT protocol further reduced tumor growth by another approximate 50%.

Example 7A

Syrian hamsters bearing transplanted orthotopic pancreatic tumors (HapT1) were divided into three groups (N=12-25/group). Two groups were administered BA (2I-EtNBS) (11.25 mg/kg), either with intervention to raise the plasma glucose level (glucose bolus administration [3 g/kg body weight, administered intraperitoneally]) to at least 20% above basal levels (Glu-BA-PDT) plus insulin (10 U/kg body weight) for a period starting about 60 minutes prior to PDT and about 4 hours after BA administration or another group without such metabolic treatment. A third group was untreated to serve as a negative control. Each of the BA groups received PDT (130 mW/cm$^2$ and 130 J/cm$^2$ of 652 nm light) 5 hours after the administration of BA. Tumor growth was assessed by measuring tumor volume at 21 days post-BA-PDT treatment. Relative to the untreated control group (tumor volume=983 mm$^3$), the tumor volume of the BA-PDT group was approximately 43% smaller. However, the tumor volume of the BA-PDT plus glucose and insulin group (GluBA-PDT plus insulin) was 55% smaller than the BA-PDT group. In other words, the tumor growth promoting intervention of adding the glucose plus insulin to the BA-PDT protocol further reduced tumor growth by another 55%.

The results of Example 7A are shown below—values are for tumor volume in mm$^3$.

25). Two groups were administered BA (2I-EtNBS) (11.25 mg/kg), either with intervention to raise the plasma glucose level (glucose bolus administration [3 g/kg body weight, administered intraperitoneally]) to at least 20% above basal levels (Glu-BA-PDT) for a period starting from 60 minutes prior to BA-PDT photoirradiation and at 4 hours after BA administration or another group without such metabolic treatment. A third group was untreated to serve as a negative control. Each of the BA groups received PDT (130 mW/cm$^2$ and 130 J/cm$^2$ of 652 nm light) 5 hours after the administration of BA. Tumor growth was assessed by measuring tumor volume at 21 days post-BA-PDT treatment. Relative to the untreated control group (tumor volume=983 mm3),

| Vehicle tumor volume (mm3) | | | PDT | | | PDT + Glu&INS tumor volume (mm3) | | | |
|---|---|---|---|---|---|---|---|---|---|
| Hamster # | Day 0 | Day 21 | Difference | Hamster # | Day 0 | Day 21 | Difference | Hamster # | Day 0 | Day 21 | Difference |
| 1020119 | 31.76 | 1212.95 | 1181.19 | 12071619 | 57.86 | 0.00 | −57.86 | 1071619 | 69.59 | 346.89 | 277.29 |
| 13020119 | 72.36 | 647.27 | 574.92 | 13071619 | 54.49 | 0.00 | −54.49 | 2071619 | 99.79 | 88.62 | −11.17 |
| 2020119 | 42.57 | 1168.87 | 1126.30 | 12072319 | 109.13 | 36.34 | −72.79 | 3071619 | 36.96 | 0.00 | −36.96 |
| 14020119 | 45.13 | 1931.76 | 1886.62 | 13072319 | 93.99 | 971.37 | 877.38 | 1072319 | 36.73 | 69.89 | 33.16 |
| 1030119 | 65.07 | 1304.41 | 1239.34 | 1080619 | 103.68 | 1417.91 | 1314.23 | 2072319 | 62.31 | 26.39 | −35.92 |
| 2030119 | 83.56 | 2034.18 | 1950.62 | 3080619 | 92.89 | 287.83 | 194.95 | 3072319 | 64.32 | 53.59 | −10.73 |
| 14030119 | 48.98 | 771.92 | 722.94 | 5080619 | 136.78 | 306.80 | 170.02 | 2082919 | 63.13 | 743.50 | 680.36 |
| 15030119 | 44.70 | 1226.70 | 1182.00 | 6080619 | 216.51 | 624.31 | 407.80 | 4082919 | 102.80 | 206.09 | 103.29 |
| 1030819 | 78.40 | 1376.74 | 1298.34 | 7080619 | 157.17 | 226.04 | 68.86 | 6082919 | 157.01 | 697.34 | 540.33 |
| 2030819 | 79.97 | 323.82 | 243.84 | 8080619 | 91.65 | 502.58 | 410.93 | 8082919 | 93.67 | 288.82 | 195.15 |
| 14030819 | 59.07 | 321.60 | 262.53 | 9080619 | 94.91 | 298.52 | 203.61 | 10082919 | 112.66 | 91.94 | −20.73 |
| 15030819 | 47.85 | 964.75 | 916.90 | 10080619 | 102.08 | 513.57 | 411.67 | 12082919 | 95.51 | 85.26 | −10.25 |
| 15071619 | 60.32 | 783.18 | 722.86 | 11080619 | 262.84 | 931.00 | 668.16 | | | | |
| 14072319 | 67.32 | 1236.52 | 1169.20 | 12080619 | 97.97 | 619.41 | 521.44 | | | | |
| 15072319 | 31.63 | 111.08 | 79.44 | 13080619 | 127.20 | 1699.25 | 1572.05 | | | | |
| 1081219 | 97.02 | 680.22 | 583.20 | 14080619 | 198.51 | 274.42 | 75.91 | | | | |
| 2081219 | 112.84 | 624.28 | 511.44 | 15080619 | 105.77 | 755.74 | 649.97 | | | | |
| 3081219 | 103.84 | 1793.68 | 1689.84 | | | | | | | | |
| 4081219 | 106.87 | 1786.72 | 1679.85 | | | | | | | | |
| 5081219 | 103.09 | 311.92 | 208.83 | | | | | | | | |
| 6081219 | 88.36 | 1112.49 | 1024.13 | | | | | | | | |
| 7081219 | 80.94 | 942.80 | 861.86 | | | | | | | | |
| 8081219 | 89.27 | 717.23 | 627.96 | | | | | | | | |
| 9081219 | 61.97 | 887.47 | 825.50 | | | | | | | | |
| 10081219 | 77.48 | 612.15 | 534.68 | | | | | | | | |
| Average | 62.86 | 983.55 | 920.69 | Average | 123.73 | 556.78 | 433.05 | Average | 76.96 | 248.03 | 171.07 |

Figure 3:
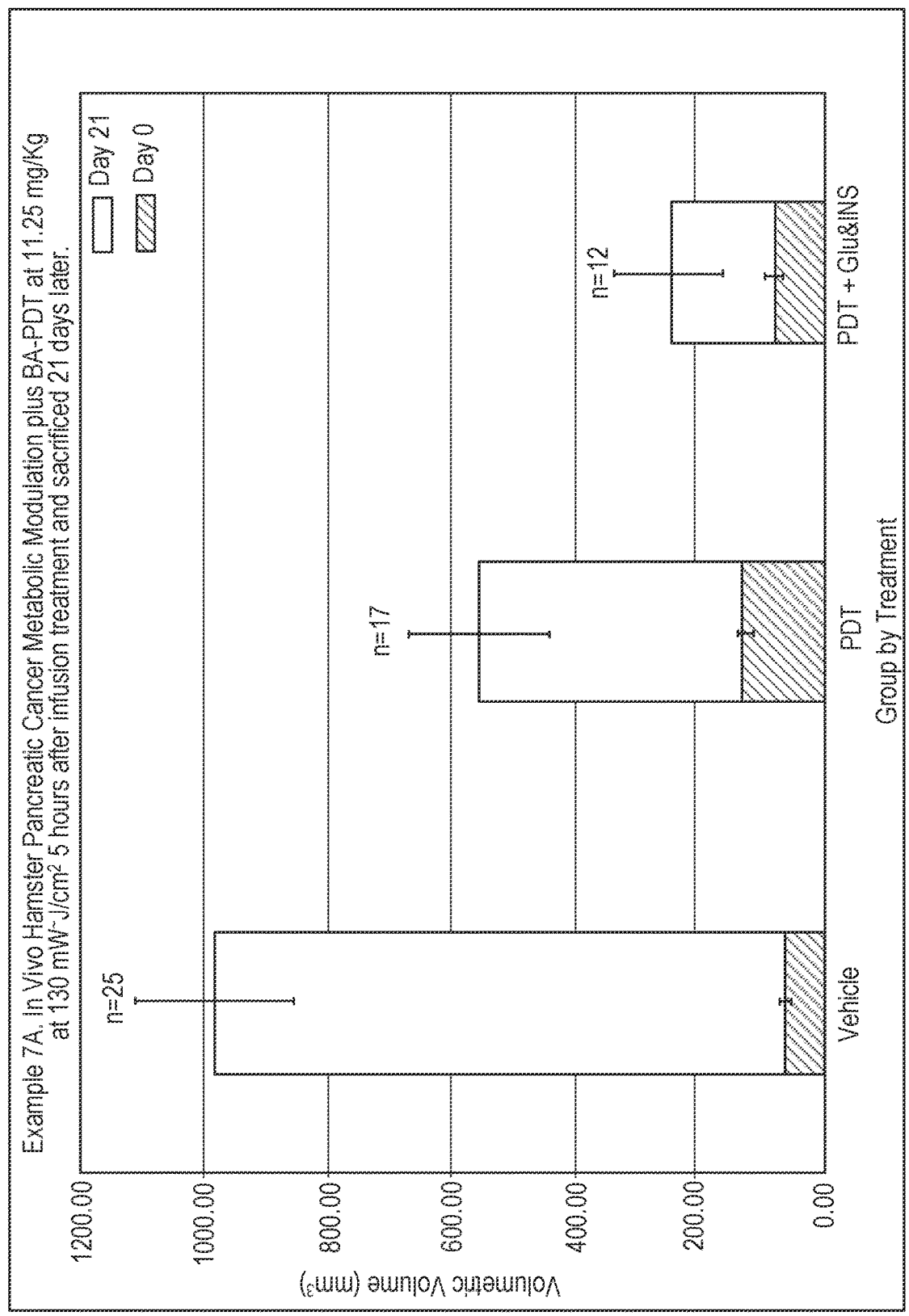
FIG. 3 is a chart illustrating the anti-tumor effect of in vivo Hamster Pancreatic Cancer Metabolic Modulation plus BA-PDT at 11.25 mg/kg at 130 mW~J/cm² at 5 hours after BA infusion treatment and sacrificed 21 days later.

FIG. 3 is a chart of Example 7A illustrating the in vivo Hamster Pancreatic Cancer Metabolic Modulation plus BA-PDT at 11.25 mg/kg at 130 mW~J/cm$^2$ 5 hours after infusion treatment and sacrificed 21 days later.

Example 7B

Syrian hamsters bearing transplanted orthotopic pancreatic tumors (HapT1) were divided into three groups (N=8- the tumor volume of the BA-PDT group was approximately 43% smaller. However, the tumor volume of the BA-PDT plus glucose (GluBA-PDT) group was 97% smaller than the BA-PDT group. In other words, the tumor growth promoting intervention of adding the glucose to the BA-PDT protocol further reduced tumor growth by another approximate 97%.

The results of Example 7B are shown below—values are for tumor volume in mm$^3$.

| Vehicle tumor volume (mm3) | | | | PDT | | | | PDT + Glu tumor volume (mm3) | | | |
|---|---|---|---|---|---|---|---|---|---|---|---|
| Hamster # | Day 0 | Day 21 | Difference | Hamster # | Day 0 | Day 21 | Difference | Hamster # | Day 0 | Day 21 | Difference |
| 1020119 | 31.76 | 1212.95 | 1181.19 | 12071619 | 57.86 | 0.00 | −57.86 | 5071619 | 73.72 | 0.00 | −73.72 |
| 13020119 | 72.36 | 647.27 | 574.92 | 13071619 | 54.49 | 0.00 | −54.49 | 7071619 | 46.04 | 0.00 | −46.04 |
| 2020119 | 42.57 | 1168.87 | 1126.30 | 12072319 | 109.13 | 36.34 | −72.79 | 9071619 | 29.79 | 0.00 | −29.79 |
| 14020119 | 45.13 | 1931.76 | 1886.62 | 13072319 | 93.99 | 971.37 | 877.38 | 11071619 | 74.00 | 106.02 | 32.03 |
| 1030119 | 65.07 | 1304.41 | 1239.34 | 1080619 | 103.68 | 1417.91 | 1314.23 | 5072319 | | 0.00 | −14.40 |
| 2030119 | 83.56 | 2034.18 | 1950.62 | 3080619 | 92.89 | 287.83 | 194.95 | 7072319 | 14.40 | 0.00 | −50.72 |
| 14030119 | 48.98 | 771.92 | 722.94 | 5080619 | 136.78 | 306.80 | 170.02 | 9072319 | 50.72 | 0.00 | −64.28 |
| 15030119 | 44.70 | 1226.70 | 1182.00 | 6080619 | 216.51 | 624.31 | 407.80 | 11072319 | 64.28 | 37.38 | 14.94 |
| 1030819 | 78.40 | 1376.74 | 1298.34 | 7080619 | 157.17 | 226.04 | 68.86 | | 22.45 | | |
| 2030819 | 79.97 | 323.82 | 243.84 | 8080619 | 91.65 | 502.58 | 410.93 | | | | |

-continued

| Vehicle tumor volume (mm3) | | | PDT | | | PDT + Glu tumor volume (mm3) | | | |
|---|---|---|---|---|---|---|---|---|---|
| Hamster # | Day 0 | Day 21 | Difference | Hamster # | Day 0 | Day 21 | Difference | Hamster # | Day 0 | Day 21 | Difference |
| 14030819 | 59.07 | 321.60 | 262.53 | 9080619 | 94.91 | 298.52 | 203.61 | | | | |
| 15030819 | 47.85 | 964.75 | 916.90 | 10080619 | 102.08 | 513.75 | 411.67 | | | | |
| 15071619 | 60.32 | 783.18 | 722.86 | 11080619 | 262.84 | 931.00 | 668.16 | | | | |
| 14072319 | 67.32 | 1236.52 | 1169.20 | 12080619 | 97.97 | 619.41 | 521.44 | | | | |
| 15072319 | 31.63 | 111.08 | 79.44 | 13080619 | 127.20 | 1699.25 | 1572.05 | | | | |
| 1081219 | 97.02 | 680.22 | 583.20 | 14080619 | 198.51 | 274.42 | 75.91 | | | | |
| 2081219 | 112.84 | 624.28 | 511.44 | 15080619 | 105.77 | 755.74 | 649.97 | | | | |
| 3081219 | 103.84 | 1793.68 | 1689.84 | | | | | | | | |
| 4081219 | 106.87 | 1786.72 | 1679.85 | | | | | | | | |
| 5081219 | 103.09 | 311.92 | 208.83 | | | | | | | | |
| 6081219 | 88.36 | 1112.49 | 1024.13 | | | | | | | | |
| 7081219 | 80.94 | 942.80 | 861.86 | | | | | | | | |
| 8081219 | 89.27 | 717.23 | 627.96 | | | | | | | | |
| 9081219 | 61.97 | 887.47 | 825.50 | | | | | | | | |
| 10081219 | 77.48 | 612.15 | 534.68 | | | | | | | | |
| Average | 62.86 | 983.55 | 920.69 | Average | 123.73 | 556.78 | 433.05 | Average | 46.92 | 17.93 | −29.00 |

Figure 4:
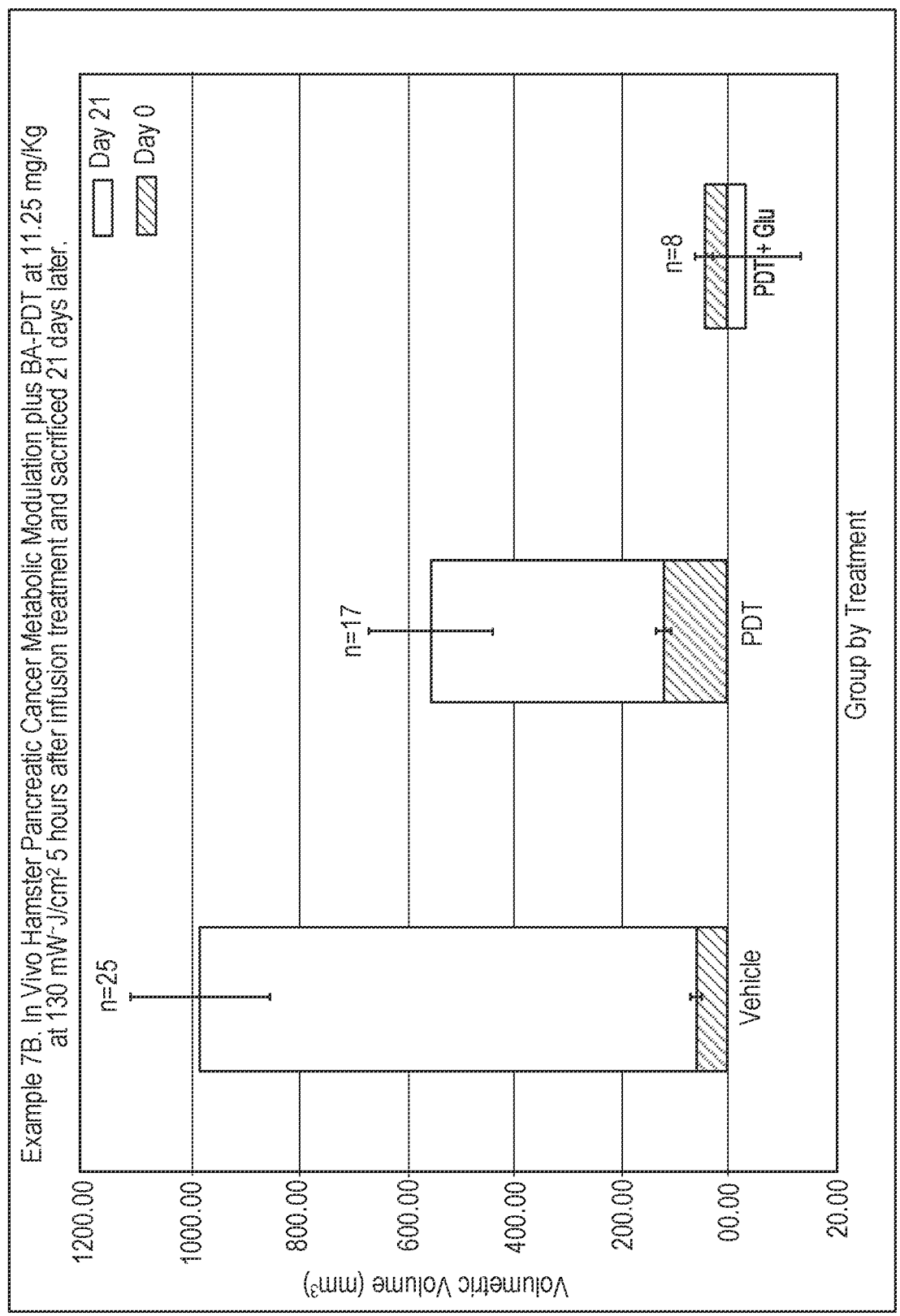
FIG. 4 is a chart illustrating the anti-tumor effect of in vivo Hamster Pancreatic Cancer Metabolic Modulation plus BA-PDT at 11.25 mg/kg at 130 mW~J/cm² at 5 hours after BA infusion treatment and sacrificed 21 days later.

FIG. 4 is a chart of Example 7B illustrating the in vivo Hamster Pancreatic Cancer Metabolic Modulation plus BA-PDT at 11.25 mg/kg at 130 mW~J/cm² at 5 hours after infusion treatment and sacrificed 21 days later.

Example 7C

Syrian hamsters bearing transplanted orthotopic pancreatic tumors (HapT1) were divided into three groups (N=7-25). Two groups were administered BA (2I-EtNBS) (11.25 mg/kg), either with intervention to raise the plasma insulin level by at least 10% (10 U/kg body weight) for a period starting about 60 minutes prior to PDT and about 4 hours after BA administration or another group without such hormonal/metabolic treatment. A third group was untreated to serve as a negative control. Each of the BA groups received PDT (130 mW/cm² and 130 J/cm² of 652 nm light) 5 hours after the administration of BA. Tumor growth was assessed by measuring tumor volume at 21 days post-BA-PDT treatment. Relative to the untreated control group (tumor volume=983 mm³), the tumor volume of the BA-PDT group was approximately 43% smaller. However, the tumor volume of the BA-PDT plus insulin group was 94% smaller than the BA-PDT group. In other words, the tumor growth promoting intervention of adding the glucose plus insulin to the BA-PDT protocol further reduced tumor growth by another 94%.

The results of Example 7C are shown below-values are for tumor volume in mm³.

| Vehicle tumor volume (mm3) | | | | PDT tumor volume (mm3) | | | | PDT + INS tumor volume (mm3) | | | |
|---|---|---|---|---|---|---|---|---|---|---|---|
| Hamster # | Day 0 | Day 21 | Difference | Hamster # | Day 0 | Day 21 | Difference | Hamster # | Day 0 | Day 21 | Difference |
| 1020119 | 3176 | 1212.95 | 1181.19 | 12071619 | 57.86 | 0.00 | −57.86 | 4071619 | 69.71 | 0.00 | −69.71 |
| 13020119 | 72.36 | 647.27 | 574.92 | 13071619 | 54.49 | 0.00 | −54.49 | 6071619 | 60.97 | 228.27 | 167.29 |
| 2020119 | 42.57 | 1168.87 | 1126.30 | 12072319 | 109.13 | 36.34 | −72.79 | 8071619 | 77.95 | 0.00 | −77.95 |
| 14020119 | 45.13 | 1931.76 | 1886.62 | 13072319 | 93.99 | 971.37 | 877.38 | 10071619 | 100.16 | 0.00 | −100.16 |
| 1030119 | 65.07 | 1304.41 | 1239.34 | 1080619 | 103.68 | 1417.91 | 1314.23 | 4072319 | 69.04 | 0.00 | −69.04 |
| 2030119 | 83.56 | 2034.18 | 1950.62 | 3080619 | 92.89 | 287.83 | 194.95 | 6072319 | 116.30 | 0.00 | −116.30 |
| 14030119 | 48.98 | 771.92 | 722.94 | 5080619 | 136.78 | 306.80 | 170.02 | 8072319 | 76.70 | 0.00 | −76.70 |
| 15030119 | 44.70 | 1226.70 | 1182.00 | 6080619 | 216.51 | 624.31 | 407.80 | | | | |
| 1030819 | 78.40 | 1376.74 | 1298.34 | 7080619 | 157.17 | 226.04 | 68.86 | | | | |
| 2030819 | 79.97 | 323.82 | 243.84 | 8080619 | 91.65 | 502.58 | 410.93 | | | | |
| 14030819 | 59.07 | 321.60 | 262.53 | 9080619 | 94.91 | 298.52 | 203.61 | | | | |
| 15030819 | 47.85 | 964.75 | 916.90 | 10080619 | 102.08 | 513.75 | 411.67 | | | | |
| 15071619 | 60.32 | 783.18 | 722.86 | 11080619 | 262.84 | 931.00 | 668.16 | | | | |
| 14072319 | 67.32 | 1236.52 | 1169.20 | 12080619 | 97.97 | 619.41 | 521.44 | | | | |
| 15072319 | 31.63 | 111.08 | 79.44 | 13080619 | 127.20 | 1699.25 | 1572.05 | | | | |
| 1081219 | 97.02 | 680.22 | 583.20 | 14080619 | 198.51 | 274.42 | 75.91 | | | | |
| 2081219 | 112.84 | 624.28 | 511.44 | 15080619 | 105.77 | 755.74 | 649.97 | | | | |
| 3081219 | 103.84 | 1793.68 | 1689.84 | | | | | | | | |
| 4081219 | 106.87 | 1786.72 | 1679.85 | | | | | | | | |
| 5081219 | 103.09 | 311.92 | 208.83 | | | | | | | | |
| 6081219 | 88.36 | 1112.49 | 1024.13 | | | | | | | | |
| 7081219 | 80.94 | 942.80 | 861.86 | | | | | | | | |
| 8081219 | 89.27 | 717.23 | 627.96 | | | | | | | | |
| 9081219 | 61.97 | 887.47 | 825.50 | | | | | | | | |
| 10081219 | 77.48 | 612.15 | 534.68 | | | | | | | | |
| Average | 62.86 | 983.55 | 920.69 | Average | 123.73 | 556.78 | 433.05 | Average | 81.55 | 32.61 | −48.94 |

Figure 5:
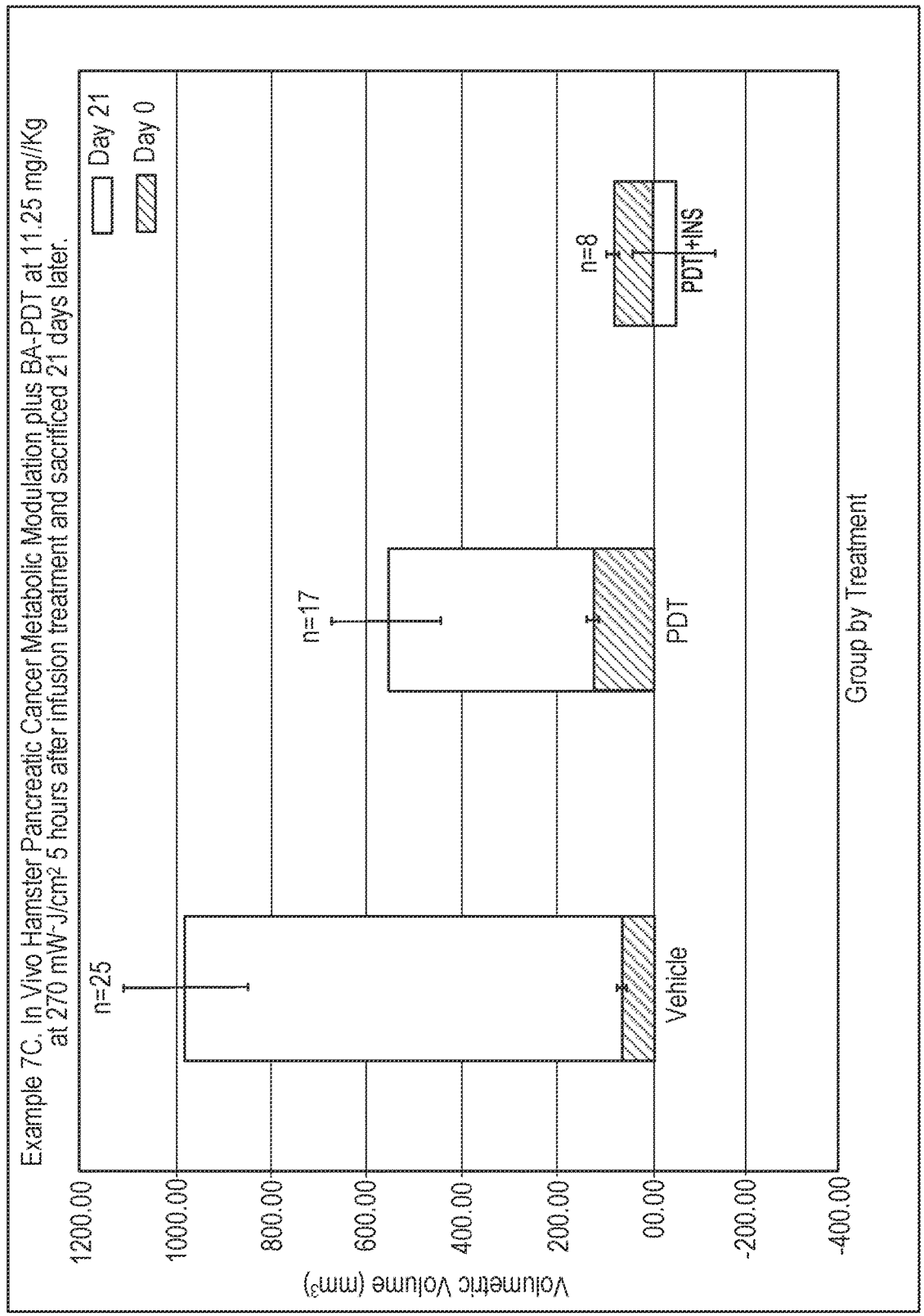
FIG. 5 is a chart illustrating the anti-tumor effect of in vivo Hamster Pancreatic Cancer Metabolic Modulation plus BA-PDT at 11.25 mg/kg at 130 mW~J/cm² at 5 hours after BA infusion treatment and sacrificed 21 days later.

FIG. 5 is a chart of example 7C illustrating the in vivo Hamster Pancreatic Cancer Metabolic Modulation plus BA-PDT at 11.25 mg/kg at 130 mW~J/cm² 5 hours after infusion treatment and sacrificed 21 days later.

Example 8

Syrian hamsters bearing transplanted orthotopic pancreatic tumors (HapT1) were divided into three groups (N=5-

9/group). Two groups were administered BA (2I-EtNBS) (11.25 mg/kg), either with intervention to raise the plasma glucose level (glucose bolus administration [3 g/kg body weight, administered intraperitoneally]) to at least 20% above basal levels (Glu-BA-PDT) plus insulin (10 U/kg body weight) for a period starting about 60 minutes prior to PDT and about 4 hours after BA administration or another group without such metabolic treatment. A third group was untreated to serve as a negative control. Each of the BA groups received PDT (270 mW/cm$^2$ and 270 J/cm$^2$ of 652 nm light) 5 hours after the administration of BA. Tumor growth was assessed by measuring tumor volume at 28 days post-BA-PDT treatment. Relative to the untreated control group (tumor volume=1750 mm$^3$), the tumor volume of the BA-PDT group was approximately 43% smaller. However, the tumor volume of the BA-PDT plus glucose and insulin group (GluBA-PDT plus insulin) was 50% smaller than the BA-PDT group. In other words, the tumor growth promoting intervention of adding the glucose plus insulin to the BA-PDT protocol further reduced tumor growth by another 50%.

Example 9

Wistar rats bearing transplanted subcutaneous bladder tumors (~5-9 mm diameter) (NBT II, from approximately 2.5 million cells injected) were divided into three groups (N=3 per group). Two groups were administered BA (2I-EtNBS) (10.0 mg/kg), either with concurrent intervention to raise the plasma glucose level (glucose bolus administration [3 g/kg body weight, administered intraperitoneally]) to at least 20% above basal levels (Glu-BA-PDT) plus insulin (1.0 U/kg body weight) at 1.5 hours after BA administration and for a period from 60 minutes before BA-PDT photoirradiation or another group without such metabolic treatment. A third group was untreated to serve as a negative control. Each of the BA groups received PDT (180 mW/cm$^2$ and 180 J/cm$^2$ of 652 nm light) 2.5 hours after the administration of BA. The tumor presence at 48 hours following PDT was 100% in the negative control group (no PDT), 67% in the BA-PDT group, and 0% in the GluBA-PDT plus insulin group. In other words, the tumor growth promoting intervention of adding the glucose plus insulin to the BA-PDT protocol further reduced tumor eradication by another approximate 67%, resulting in 100% of animals tumor free at this time point.

Example 10

Fischer 344 rats bearing transplanted subcutaneous brain tumors (glioma) (~5-9 mm diameter) (9 L tumor cells, from approximately 2.0-2.5 million cells injected) were divided into three groups (N=3 per group). Two groups were administered BA (2I-EtNBS) (10.0 mg/kg), either with concurrent intervention to raise the plasma glucose level (glucose bolus administration [3 g/kg body weight, administered intraperitoneally]) to at least 20% above basal levels (Glu-BA-PDT) plus insulin (1.0 U/kg body weight) at 1.5 hours after BA administration and for a period from 60 minutes before BA-PDT photoirradiation or another group without such metabolic treatment. A third group was untreated to serve as a negative control. Each of the BA groups received PDT (180 mW/cm$^2$ and 180 J/cm$^2$ of 652 nm light) 2.5 hours after the administration of BA. The tumor presence at 35 days following PDT was 67% in the negative control group (no PDT), 50% in the BA-PDT group, and 0% in the GluBA-PDT plus insulin group. In other words, the tumor growth promoting intervention of adding the glucose plus insulin to the BA-PDT protocol further reduced tumor eradication by another approximate 50%.

Example 11

Animals bearing tumors of ectodermal, endodermal, or mesodermal origin (~5-9 mm diameter) are divided into three groups. Two groups are administered 2I-EtNBS (BA) (6-12 mg/kg), either with treatment that increases the metabolic activity of the animals (feeding, [particularly a high fat and/or sugar/carbohydrate diet], metabolic activity increasing hormones such as insulin, growth hormone, thyroid hormones, corticosteroids, or a combination of such feeding and hormonal intervention) to raise the metabolic activity level to at least 10% above basal level for a period of time at least 30 minutes prior to BA administration and extending to as much as 60 minutes after BA-PDT administration or another group without such concurrent metabolic activity increasing intervention. A third group is untreated to serve as a negative control. Each of the BA groups receive PDT (exposure to 100 mW/cm$^2$ and 100 J/cm$^2$ of 652 nm light) 5 hours after the administration of BA. Relative to the BA-PDT group, the decrease in tumor size in the metabolic activity increasing-BA-PDT group at 21 days post-PDT is predicted to be significantly greater than in the control and BA-PDT groups.

In all examples above, administration to several groups of animals of the metabolism altering methods (e.g., GluBA-PDT, MetabBA-PDT or FFA-BA-PDT with or without insulin) without concurrent application of BA-PDT had no effect on tumor regression or eradication. That is such metabolic treatments in and of themselves produced no change in tumor volume at the study endpoints versus the vehicle controls. Consequently, the above described observations demonstrate the presence of a synergistic interaction between BA-PDT and the metabolism-altering methods (i.e., raising the plasma glucose and/or FFA level or metabolic activity and/or inducing hormonal changes (e.g., insulin administration) as described herein). That is, the effect of combining a metabolism-altering method (individual anti-tumor effect=0) with BA-PDT (individual anti-tumor effect=X) is greater than the expected additive effect of combining the two (i.e., the actual/observed effect is >>X, whereas the theoretical additive effect would be 0+X=X). In cases where the BA-PDT treatment did not produce a difference from the vehicle control in terms of tumor volume, (and neither did the metabolism altering methods), the metabolism altering methods plus BA-PDT did so.

In fact, it is generally observed that raising the plasma glucose and/or FFA level and/or inducing insulin resistance in tumor-bearing organisms not only does not have any anti-tumor effect but actually increases tumor growth rate via various mechanisms including providing fuel and growth stimulating hormones (insulin) for tumor growth that can inhibit immune system function against the tumor (i.e., anti-tumor effect <0). Thus, it would have been counterintuitive to combine BA-PDT (intended to treat cancer) with one or more of these metabolism-altering methods (which by themselves are known to actually enhance tumor growth). Moreover, the tumor eradication rate at study endpoint (no visible tumor present) can be greater among animals treated with BA-PDT plus metabolic activity increasing methods described herein versus BA-PDT alone.

Addition of Circadian Neuroendocrine Resetting Therapy to the Metabolic Activity Altering-BA-PDT Method to Treat Cancer It is known that circadian rhythms of neuroendocrine activity can influence immune function in the body. Several aspects of immune function themselves exhibit circadian or diurnal activity. Cancer (tumor cell growth) has the capacity to disrupt both neuroendocrine and immune circadian organization of immune function thus leading to a diminished ability of the immune system to combat or attenuate cancer growth. It has now been found that the metabolism altering activity-BA-PDT approaches described herein can be further enhanced to inhibit tumor growth by appropriate circadian timed administration of dopaminergic agonists (e.g., bromocriptine, dihydroergocriptine, dihydroergotoxine [hydergine], dopamine D1 agonists such benzazepine analogs) at 0.001 to 1 mg/kg BW, and prolactin stimulating compounds (e.g., prolactin [at 0.01 to 100 ug/kg BW], or melatonin, tryptophan, 5-hydroxy-tryptophan [at 0.01 ug to 10 mg/kg/BW]). The dopamine agonist is administered at a time of day so as to effectuate a daily peak in brain dopaminergic activity that coincides with the natural circadian peak in such activity in healthy individuals without cancer (generally within about 4 hours of waking from the daily sleep cycle, preferably within about 2 hours of waking). The prolactin stimulating compound is administered at a time of day so as to effectuate a daily peak in plasma prolactin level that coincides with the natural circadian peak in such activity in healthy individuals without cancer (generally within about 4 hours of onset of daily sleep cycle, preferably just before the onset of sleep).

Example 12

Syrian hamsters held on 14 hour daily photoperiods and bearing transplanted orthotopic pancreatic tumors (HapT1) were divided into four groups (N=8-16/group). Two groups were administered BA (2I-EtNBS) (11.25 mg/kg), either with intervention to raise the plasma glucose level (glucose bolus administration [3 g/kg body weight, administered intraperitoneally]) to at least 20% above basal levels (GluBA-PDT) plus insulin (10 U/kg body weight) for a period starting about 60 minutes prior to PDT and about 4 hours after BA administration or another group with such metabolic treatment and additionally treatment with bromocriptine at the onset of waking (10 mg/kg BW) and prolactin (0.25 mg/kg BW) at 10 hours after the onset of sleep for a period of time 4 days before, during, and 6 days after the BA-PDT. A third group was treated only with bromocriptine at the onset of waking (10 mg/kg BW) and prolactin (0.25 mg/kg BW) at 10 hours after the onset of sleep. A fourth group was untreated to serve as a negative control. Each of the BA groups received PDT (130 mW/cm$^2$ and 130 J/cm$^2$ of 652 nm light) 5 hours after the administration of BA. Tumor growth was assessed by measuring tumor volume at 34 days post-BA-PDT treatment. Relative to the untreated control group (tumor volume=1082 mm$^3$), the tumor volume of the BA-PDT group was approximately 57% smaller. However, the tumor volume of the BA-PDT plus glucose and insulin group (GluBA-PDT plus insulin) with such bromocriptine plus prolactin treatment was 78% smaller than the GluBA-PDT plus insulin group. In other words, the tumor growth promoting intervention of adding the glucose plus insulin to the BA-PDT protocol that reduced tumor growth by 54% was further enhanced by circadian timed bromocriptine plus prolactin administration that further reduced tumor size by another 78% relative to the GluBA-PDT plus insulin group. Improvements in tumor size reduction were also observed for the GluBA-PDT plus insulin plus prolactin and the GluBA-PDT plus insulin plus bromocriptine groups relative to the GluBA-PDT plus insulin group (65% and 21% further reduction in tumor size, respectively). The bromocriptine at the onset of waking (10 mg/kg BW) and prolactin (0.25 mg/kg BW) at 10 hours after the onset of sleep group had no reduction in tumor size (1467 mm$^3$) relative to the vehicle control.

The results of Example 12 are shown in the table below-values are for tumor volume in mm$^3$.

| Vehicle | | | | PDT + Glu/INS | | | |
| --- | --- | --- | --- | --- | --- | --- | --- |
| Hamster # | Day 0 | Day 34 | Difference | Hamster # | Day 0 | Day 34 | Difference |
| 1021120 | 76.56 | 382.48 | 305.92 | 2021120 | 96.05 | 340.85 | 244.80 |
| 5021120 | 110.00 | 1280.78 | 1170.78 | 6021120 | 93.21 | 418.46 | 325.25 |
| 1022020 | 164.65 | 1474.22 | 1309.57 | 2022020 | 110.94 | 261.61 | 150.66 |
| 5022020 | 33.91 | 953.76 | 919.85 | 6022020 | 48.57 | 913.03 | 864.46 |
| 1022520 | 37.88 | 906.52 | 868.64 | 2022520 | 91.36 | 0.00 | −91.36 |
| 5022520 | 53.60 | 1026.53 | 972.93 | 6022520 | 43.21 | 0.00 | −43.21 |
| 1030520 | 78.94 | 1474.54 | 1395.60 | 2030520 | 88.97 | 459.56 | 370.58 |
| 5030520 | 79.81 | 727.81 | 648.00 | 6030520 | 150.64 | 0.00 | −150.64 |
| 1031020 | 109.72 | 1207.30 | 1097.58 | 2031020 | 63.40 | 0.00 | −63.40 |
| 5031020 | 129.28 | 454.50 | 325.22 | 6031020 | 101.49 | 0.00 | −101.49 |
| 1042820 | 57.55 | 1285.48 | 1227.94 | 2041420 | 57.10 | 0.00 | −57.10 |
| 5042820 | 47.69 | 326.02 | 278.33 | 6041420 | 107.22 | 642.49 | 535.27 |
| 1051920 | 251.70 | 457.60 | 205.90 | 2042820 | 103.37 | 0.00 | −103.37 |
| 5051920 | 95.10 | 3197.39 | 3102.29 | 6042820 | 80.78 | 875.78 | 795.00 |
| | | | | 2051920 | 94.06 | 1010.62 | 916.57 |
| | | | | 6051920 | 166.93 | 2559.28 | 2392.35 |
| Average | 94.74 | 1082.5 | 987.75 | Average | 93.58 | 467.61 | 374.02 |

| Vehicle + Pro/BC | | | | PDT + Glu/INS + Pro/BC | | | |
| --- | --- | --- | --- | --- | --- | --- | --- |
| Hamster # | Day 0 | Day 34 | Difference | Hamster # | Day 0 | Day 34 | Difference |
| 3031020 | 59.99 | 0.00 | −59.99 | 4031020 | 51.41 | 0.00 | 0.00 |
| 7031020 | 64.08 | 107.34 | 43.27 | 8031020 | 94.05 | 0.00 | −94.05 |
| 9031020 | 77.71 | 6884.61 | 6806.90 | 10031020 | 94.90 | 453.65 | 358.76 |
| 11031020 | 47.66 | 2165.22 | 2117.56 | 12031020 | 75.23 | 0.00 | −75.23 |
| 3041420 | 10.12 | 42.26 | 32.14 | 4041420 | 89.17 | 0.00 | −89.17 |
| 7041420 | 100.16 | 1744.99 | 1644.84 | 8041420 | 87.27 | 0.00 | −87.27 |
| 9041420 | 61.89 | 441.89 | 380.00 | 10041420 | 119.32 | 52.46 | −66.86 |

-continued

| 11041420 | 92.87 | 356.61 | 263.74 | 12041420 | 107.81 | 337.85 | 230.03 |
| Average | 64.31 | 1467.87 | 1403.56 | Average | 89.89 | 105.50 | 22.03 |

Figure 6:
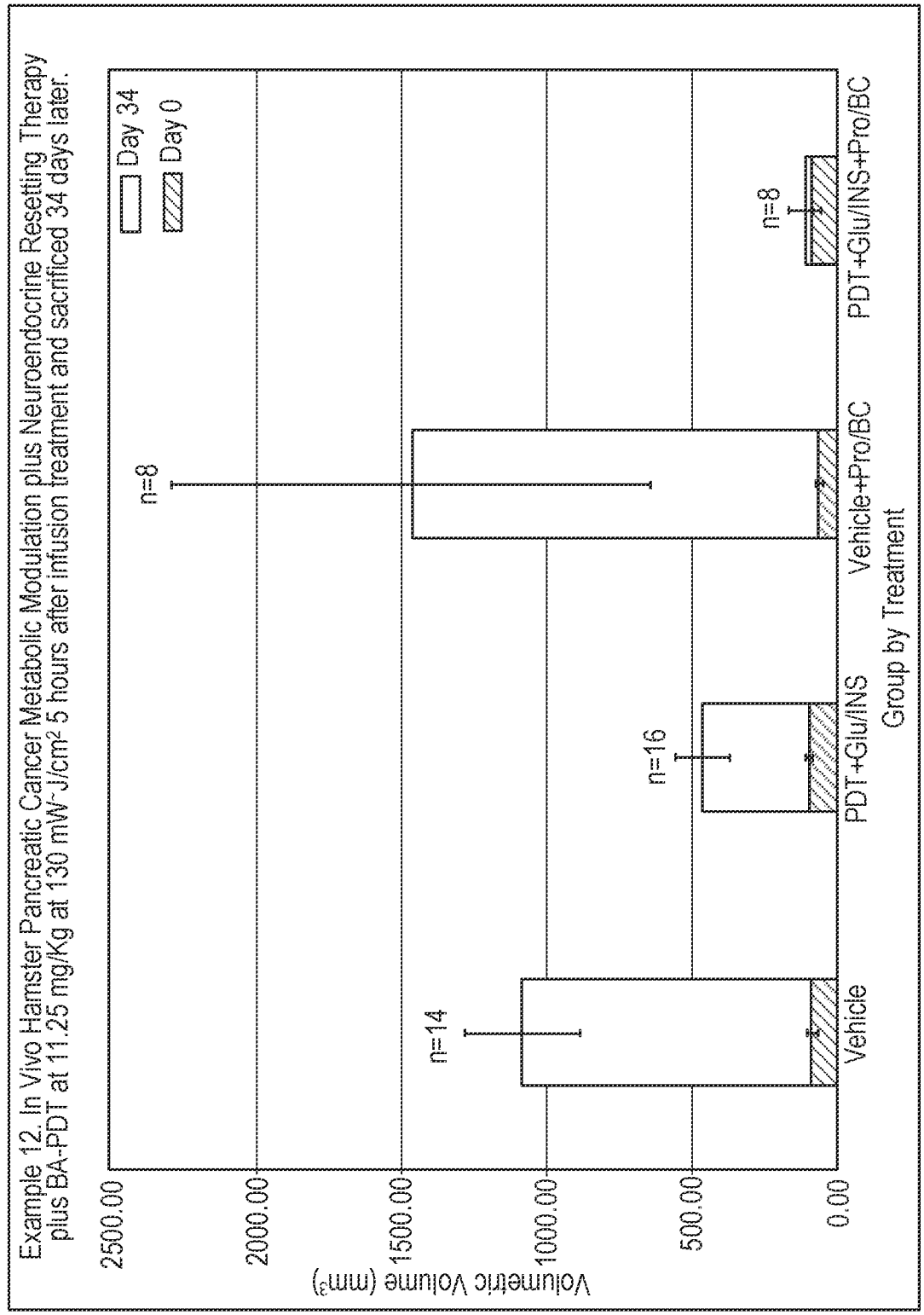
FIG. 6 is a chart a chart illustrating the anti-tumor effect of in vivo Hamster Pancreatic Cancer Metabolic Modulation plus Neuroendocrine Resetting Therapy plus BA-PDT at 11.25 mg/kg at 130 mW~J/cm² at 5 hours after BA infusion treatment and sacrificed 34 days later.

FIG. 6 is a chart a chart of Example 12 illustrating in vivo Hamster Pancreatic Cancer Metabolic Modulation plus Neuroendocrine Resetting Therapy plus BA-PDT at 11.25 mg/kg at 130 mW~J/cm² 5 hours after infusion treatment and sacrificed 34 days later.

Animals bearing tumor are treated with BA-PDT as follows:
- Administration of EtNBSI at 7.5-11.25 mg/kg body weight in an acidified aqueous solution of 3-10% sucrose via intravenous infusion of the EtNBSI solution, at a total infusion volume equal to one-quarter of the animal's total blood volume at a rate that creates a plasma BA $T_{max}$ within about 10 to 360 minutes following termination of infusion, followed by a plasma level less than about 50% of the $T_{max}$ level within about 10 to 360 minutes following the initial $T_{max}$ time.
- Irradiation of the tumor mass within about 30 to 24 hours following the termination of EtNBSI infusion with "red" light (i.e., light with a wavelength between about 600 and 700 nm, preferably >620 nm at 50-300 Mw/cm² and 50-300 J/cm².
- Such treated animals demonstrate a superior PDT effect relative to animals treated with either a more concentrated solution (i.e., smaller volume) of the BA, or with a slower infusion time of BA, or animals treated with BA in a manner that does not produce the above described pharmacokinetic BA profile.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All patent applications, patents, and other publications cited herein are incorporated by reference in their entireties.

What is claimed is:

1. A method of treating a malignant brain tumor in a subject comprising:
   1) administering at least one of glucose, glucagon, corticosteroids, growth hormones, thyroid hormones and insulin, to the subject until the plasma glucose level of the subject is above the basal plasma glucose of the subject;
   2) administering at least one EtNBS compound to the subject; and thereafter
   3) exposing the subject to actinic light.

2. The method of claim 1 wherein the malignant tumor is a glioma.

3. The method of claim 2 wherein the glioma is a glioblastoma.

4. The method of claim 1, comprising administering glucose to the subject.

5. The method of claim 1, comprising administering one or more hormones to the subject.

6. The method of claim 1, comprising waiting at least 30 minutes between administration of the EtNBS compound to the subject and exposing the subject to actinic light.

7. The method of claim 1 comprising increasing the plasma glucose level of the subject by at least 10,15, 20, 25, 30, 35, 40, 45 or 50% above the basal plasma glucose level of the subject.

8. The method of claim 1 wherein the actinic light comprises light in the range of wavelength 600-700 nm.

9. The method of claim 1 which comprises administering to the subject between about 0.01 to 15 mg/kg of body weight of at least one EtNBS compound.

10. The method of claim 6 wherein the actinic light comprises laser light.

11. The method of claim 1 wherein the actinic light delivers total light energy of between about 50 and about 500 Joules (J)/cm2.

12. The method of claim 1 wherein the power density of the light is between about 50 and 500 mW/cm.

13. The method of claim 1 wherein the time period after glucose administration and exposure to actinic light is about 30 to 60 minutes.

14. The method of claim 1 comprising administering glucagon to the subject.

15. The method of claim 1 comprising administering corticosteroids to the subject.

16. The method of claim 1 comprising administering growth hormones to the subject.

17. The method of claim 1, comprising administering thyroid hormones to the subject.

18. The method of claim 1, comprising administering insulin to the subject.

19. The method of claim 1, comprising administering glucose and insulin to the subject.

20. The method of claim 1 wherein the EtNBS compound is 2-iodo-5-ethylamino-9-diethylamino-benzo [a]phenothiazinium chloride.

* * * * *